United States Patent
Göblyös et al.

(10) Patent No.: US 9,326,978 B2
(45) Date of Patent: May 3, 2016

(54) A3 ADENOSINE RECEPTOR ALLOSTERIC MODULATORS

(71) Applicants: Anikó Göblyös, Ujszasz (HU);
Johannes Brussee, Rijnsburg (NL);
Adriaan P. Ijzerman, Haarlem (NL);
Zhan-Guo Gao, Rockville, MD (US);
Kenneth Jacobson, Silver Spring, MD (US)

(72) Inventors: Anikó Göblyös, Ujszasz (HU);
Johannes Brussee, Rijnsburg (NL);
Adriaan P. Ijzerman, Haarlem (NL);
Zhan-Guo Gao, Rockville, MD (US);
Kenneth Jacobson, Silver Spring, MD (US)

(73) Assignees: The United States of America, Represented by the Secretary, Dept. of Health and Human Services, Washington, DC (US); Universiteit Leiden, Leiden (NL)

( * ) Notice: Subject to any disclaimer, the term of this patent is extended or adjusted under 35 U.S.C. 154(b) by 197 days.

(21) Appl. No.: 13/800,560

(22) Filed: Mar. 13, 2013

(65) Prior Publication Data

US 2013/0197025 A1 Aug. 1, 2013

Related U.S. Application Data

(63) Continuation of application No. 12/219,772, filed on Jul. 28, 2008, now Pat. No. 8,420,664, which is a continuation-in-part of application No. PCT/US2007/001930, filed on Jan. 25, 2007.

(60) Provisional application No. 60/762,141, filed on Jan. 26, 2006.

(51) Int. Cl.
*A61K 31/4745* (2006.01)
*A61K 31/00* (2006.01)
*C07D 471/04* (2006.01)

(52) U.S. Cl.
CPC ............ *A61K 31/4745* (2013.01); *A61K 31/00* (2013.01); *C07D 471/04* (2013.01)

(58) Field of Classification Search
CPC .................................................. C07D 471/04
USPC ............................................ 546/82; 514/293
See application file for complete search history.

(56) References Cited

U.S. PATENT DOCUMENTS

2004/0016709 A1 1/2004 Felcman et al.
2004/0137477 A1 7/2004 Fishman et al.
2006/0194756 A1 8/2006 Borea et al.

FOREIGN PATENT DOCUMENTS

| WO | 96/06084 A1 | 2/1996 |
|---|---|---|
| WO | 99/18142 A1 | 4/1999 |
| WO | 02/062801 A1 | 8/2002 |
| WO | 2005/063246 A1 | 7/2005 |
| WO | 2007/089507 A1 | 8/2007 |

OTHER PUBLICATIONS

Gao, et al., "Selective Allosteric Enhancement of Agonist Binding and Function at Human A3 Adenosine Receptors by a Series of Imidazoquinoline Derivatives", Mol. Pharmacol., vol. 62, No. 1, pp. 81-89, (2002).

Bruns, et al., "Allosteric Enhancement of Adenosine A1 Receptor Binding and Function by 2-Amino-3-benzoylthiophenes", Molecular Pharmacology, vol. 38, pp. 939-949, (1990).

Baharav, et al., "Antiinflannnnatory Effect of A3 Adenosine Receptor Agonists in Murine Autoimmune Arthritis Models", J Rheumatol, vol. 32, pp. 469-476, (2005).

Fishman, et al., "Evidence for involvement of Wnt signaling pathway in IB-MECA mediated suppression of melanoma cells", Oncogene, vol. 21, pp. 4060-4064, (2002).

Fishman, et al., "An agonist to the A3 adenosine receptor inhibits colon carcinoma growth in mice via modulation of GSK-38 and NF-κβ", Oncogene, vol. 23, pp. 2465-2471, (2004).

Gao, et al., "Allosteric Modulators of A2A Adenosine Receptors by Amiloride Analogues and Sodium Ions", Biochemical Pharmacology, vol. 60, pp. 669-676, (2000).

Gao, et al., "Site-Directed Mutagenesis Studies of Human A2A Adenosine Receptors: Involvement of GLU13 and HIS278 in Ligand Binding and Sodium Modulation", Biochemical Pharmacology, vol. 60, pp. 661-668, (2000).

Gessi, et al., "Elevated Expression of A3 Adenosine Receptors in Human Colorectal Cancer is Reflected in Peripheral Blood Cells", Clin Cancer Res., vol. 10, pp. 5895-5901, (2004).

Ohana, et al., "Inhibition of primary colon carcinoma growth and liver metastasis by the A3 adenosine receptor agonist CF101", British Journal of Cancer, vol. 89, pp. 1552-1558, (2003).

(Continued)

*Primary Examiner* — Jeffrey S. Lundgren
*Assistant Examiner* — Sara E Townsley
(74) *Attorney, Agent, or Firm* — Vorys, Sater, Seymour and Pease LLP

(57) ABSTRACT

The claimed subject matter relates to allosteric modulation of $A_3$ adenosine receptor ($A_3AR$) and provides for the use of an $A_3$ adenosine receptor modulator ($A_3RM$), for the preparation of pharmaceutical compositions for modulating the $A_3AR$ in a subject, as well as pharmaceutical compositions including the same and therapeutic methods including administering to a subject an amount of an $A_3RM$, the amount being effective to modulate $A_3AR$ activity. The $A_3RM$ according to claimed subject matter are 1H-Imidazo-[4,5-c]quinolin-4-amine derivatives. Also provided are 1H-Imidazo-[4,5-c]quinolin-4-amine derivatives.

6 Claims, 3 Drawing Sheets

(56) References Cited

OTHER PUBLICATIONS

Montesinos, et al., "Adenosine A2A or A3 Receptors are Required for Inhibition of Inflammation by Methotrexate and Its Analog MX-68", Arthritis & Rheumatism, vol. 48, No. 1, pp. 240-247, (2003).

Madi, et al., "The A3 Adenosine Receptor is Highly Expressed in Tumor versus Normal Cells: Potential Target for Tumor Growth Inhibition", Clinical Cancer Research, vol. 10, pp. 4472-4479, (2004).

Mabley, et al., "The adenosine A3 receptor agonist, N6-3-iodobenzyl)-adenosine-5'-N-methyluronamide, is protective in two murine models of colitis", European Journal of Pharmacology, vol. 66, pp. 323-329, (2003).

Madi, et al., "A3 Adenosine Receptor Activation in Melanoma Cells", The Journal of Biological Chemistry, vol. 278, No. 43, Issue of Oct. 24, pp. 42121-42130, (2003).

Szabó, et al., "Suppression of macrophage inflammatory protein (MIP)-1α production and collagen-induced arthritis by adenosine receptor agonists", British Journal of Pharmacology, vol. 125, pp. 379-387, (1998).

Ardashev, et al., "Isocyanates of the Quinoline Series", Chemistry of Heterocyclic Compounds (A Translation of Khimiyageterotsiklicheskikh Soedinenii), Plenumm Press Co., New York, NY, US, vol. 8, No. 4, Apr. 1, 1972, pp. 480-481, XP008114719, ISSN: 0009-3122.

Heitman, et al., "A Series of 2,4-Disubstituted Quinolines as a New Class of Allosteric Enhancers of the Adenosine A3 Receptor", Journal of Medicinal Chemistry, Feb. 26, 2009, vol. 52, No. 4, Feb. 2009, pp. 926-931, XP008114805, ISSN: 1520-4804.

Burger, et al., "Medicinal Chemistry", Third Edition, 1997, p. 74.

Office Action issued in the corresponding EP application No. 09 787 530.6 on Aug. 31, 2011, 5 pages.

Neuwels, "Approache d'un pharmacophore adenosine par la modélisation moléculaire", J. Pharm. Belg., vol. 47, No. 4, pp. 351-363, (1992).

Göblyös, et al., "Structure-Activity Relationships of New 1H-Imidazo[4,5-c]quinolin-4-amine Derivatives as Allosteric Enhancers of the A3 Adenosine Receptor", J. Med. Chem., vol. 49, pp. 3354-3361, (2006).

Fossa, et al., "New pyrazolo[3,4-b]pyridones as selective A1 adenosine receptor antagonists: synthesis, biological evaluation and molecular modelling studies", Org. Biomol. Chem., vol. 3, pp. 2262-2270, (2005).

van Galen, et al., "1H-Imidazo[4,5-c]quinolin-4-amines: Novel Non-Xanthine Adenosine Antagonists", J. Med. Chem., vol. 34, pp. 1202-1206, (1991).

Ijzerman, et al., "Molecular Modelling of the Antagonist Binding Site on the Adenosine A1 Receptor", Nucleosides & Nucleotides, vol. 10, No. 5, pp. 1039-1047, (1991).

Adenot, et al., "Interest of cluster significance analysis in structure-affinity relationships for non-xanthine heterocyclic antagonists of adenosine", Eur J Med Chem, vol. 32, pp. 493,504, (1997).

Fishman, et al., "Targeting the A3 Adenosine Receptor for Cancer Therapy: Inhibition of Prostate Carcinoma Cell Growth by A3AR Agonist", Anticancer Research, vol. 23, pp. 2077-2084, (2003).

A3 ADENOSINE RECEPTOR ALLOSTERIC MODULATORS

FIELD OF THE INVENTION

This invention relates to $A_3$ adenosine receptor ($A_3AR$) allosteric modulators and uses thereof.

PRIOR ART

The following is a list of prior art which is considered to be pertinent for describing the state of the art in the field of the invention. Acknowledgement of these references herein will at times be made by indicating their number within brackets from the list below.

1. Fishman P, et al. Evidence for involvement of Wnt signaling pathway in IB-MECA mediated suppression of melanoma cells. *Oncogene.*, 21:4060-4064 (2002).
2. Fishman P, et al. Targeting the A3 adenosine receptor for cancer therapy: inhibition of Prostate carcinoma cell growth by $A_3AR$ agonist. *Anticancer Res.*, 23:2077-2083 (2003).
3. Madi L, et al. A3 adenosine receptor activation in melanoma cells: association between receptor fate and tumor growth inhibition. *J. Bio. Chem.*, 278:42121-42130 (2003).
4. Ohana G, et al. Inhibition of primary colon carcinoma growth and liver metastasis by the A3 adenosine receptor agonist IB-MECA. *British J. Cancer*, 89:1552-1558 (2003).
5. Fishman P, et al. An agonist to the A3 adenosine receptor inhibits colon carcinoma growth in mice via modulation of GSK-3β and NF-κB. *Oncogene*, 23:2465-2471 (2004).
6. US Patent Application No. 2004016709 A1.
7. Szabo, C., et al. Suppression of macrophage inflammatory protein (MIP)-1α production and collagen-induced arthritis by adenosine receptor agonists. *British J. Pharmacology*, 125:379-387 (1998).
8. Mabley, J., et al. The adenosine $A_3$ receptor agonist, $N^6$-(3-iodobenzyl)-adenosine-5'-N-methyluronamide, is protective in two murine models of colitis. *Europ. J. Pharmacology*, 466:323-329 (2003).
9. Baharav, E., et al. The effect of adenosine and the $A_3$ adenosine receptor agonist IB-MECA on joint inflammation and autoimmune diseases models. *Inter. J. Mol. Med.* 10 (supplement 1) page 5104, abstract 499 (2002).
10. PCT Application, publication No. WO2005/0063246, entitled "Method for Treatment of Multiple Sclerosis".
11. Montesinos, M. Carmen, et al. Adenosine $A_{2A}$ or $A_3$ receptors are required for inhibition of inflammation by methotrexate and its analog MX-68. *Arthritis & Rheumatism*, 48:240-247 (2003).
12. Madi L, et al. The $A_3$ Adenosine Receptor is Highly Expressed in Tumor vs. Normal Cells: Potential Target for Tumor Growth Inhibition. *Clinical Cancer Research*, 10: 4472-4479 (2004).
13. US Patent Application, publication No. 20040137477 A1, entitled "A3AR as a marker for a diseased state".
14. Gessi, S. et al. Elevated expression of $A_3$ adenosine receptors in human colorectal cancer is reflected in peripheral blood cells *Clinical Cancer Research* 10:5895-5901 (2004).
15. Birdsall N J et al., Allosteric regulation of G-protein-linked receptors *biochem Soc Trans* 23:108-111 (1995).
16. Holzgrabe U and Mohr K, Allosteric modulators of ligand binding to muscarinic acetylcholine receptors, *Drug Disc Today* 3:214-222 (1998).
17. Bruns R F and Fergus J H, Allosteric enhancement of adenosine $A_1$ receptor binding and function by 2-amino-3-benzoylthiophenes, *Mol Pharmacol* 38:939-949 (1990).
18. Gao Z G and IJzerman A P, Allosteric modulation of $A_{2A}$ adenosine receptors by amiloride analogues and sodium ions, *Biochem Pharmacol* 60:669-676 (2000).
19. Gao Z G, Jiang Q, Jacobson K A, and IJzerman A P, Site-directed mutagenesis studies of human $A_{2A}$ adenosine receptors. Involvement of $Glu^{13}$ and $His^{278}$ in ligand binding and sodium modulation, *Biochem Pharmacol* 60:661-668 (2000).
20. Gao Z G, Kin S G, Soltysiak K A, Melman N, IJzerman A P, Jacobson K A, Selective allosteric enhancement of agonist binding and function at human A3 Adenosine receptors by a series of imidazoquinoline derivatives, *Mol Pharmacol* 62:81-89 (2002).

BACKGROUND OF THE INVENTION

G protein-coupled receptors (GPCRs) class is the largest family of cell-surface receptors which plays a crucial role in intracellular signal transduction. Adenosine receptors are part of the GPCR class, which belongs to the Class A or rhodopsin-like subfamily of GPCRs. Adenosine, a purine nucleoside, produces numerous physiological actions via cell surface adenosine receptors. These receptors are widely distributed throughout the body and are divided into four subclasses, $A_1$, $A_{2A}$, $A_{2B}$ and $A_3$ receptors, the latter being the most recently identified receptor.

The $A_3$ adenosine receptor ($A_3AR$) is involved in a variety of physiological processes. The receptor is highly expressed in various tumor cell types while expression in adjacent normal tissues is relatively low. Activation of the receptor by a specific synthetic agonist induces modulation of downstream signal transduction pathways which include the Wnt and the NF-kB, resulting in tumor growth inhibition (1-5).

In vivo studies have shown that $A_3AR$ agonists inhibit the development of colon, prostate and pancreatic carcinomas as well as melanoma and hepatoma. $A_3AR$ agonists were also been shown to act as anti-inflammatory agents by ameliorating the inflammatory process in different experimental autoimmune models such as rheumatoid arthritis, Crohn's disease and multiple sclerosis (6-10). It was proposed also that the $A_{2A}$ and $A_3$ receptors mediate the anti-inflammatory effects of methotrexate (11).

$A_3$ adenosine receptor ($A_3AR$) expression levels are elevated in cancer cells as compared to normal cells (12). Thus, the $A_3AR$ expression level has been described as a means for the diagnosis of cancer (13). In addition, $A_3AR$ expression levels have also been described to be elevated in peripheral blood cells of patients with colorectal cancer (14).

Several members of the GPCR class of receptors have been reported to be modulated allosterically (15), i.e. these receptors have additional binding site(s) on a receptor that are distinct from the agonist binding site (orthosteric site, orthosterically modulated receptors), but that can modulate receptor activity.

Allosteric modulation of GPCRs has been characterized most extensively for muscarinic receptors (16), and it has been suggested that allosteric modulators may provide therapeutic advantages over orthosteric agonists. Such advantages may include greater subtype selectivity and fewer side effects (15).

The adenosine receptors are natural allosteric proteins because agonist-mediated signaling by GPCRs requires a conformational change in the receptor protein transmitted between two topographically distinct binding sites, one for the agonist and another for the G protein. Allosteric sites on GPCRs represent novel drug targets because allosteric modulators possess a number of advantages over classic orthosteric ligands, such as a ceiling level to the allosteric effect and a potential for greater GPCR subtype-selectivity.

Allosteric modulation of $A_1$ adenosine receptors was reported (17). A number of aminobenzoylthiophenes, including PD81723, were allosteric modulators of the $A_1$ adenosine receptor (19). These compounds were shown to be highly subtype-selective enhancers for $A_1$ adenosine receptors (19) and were less likely to cause desensitization and down-regulation of receptors than selective $A_1$ adenosine receptor agonists.

Some 1H-imidazo-[4,5-c]quinoline derivatives were described as selective allosteric enhancers of human A3 adenosine receptors (20). Specifically, the derivatives were shown to potentiate the potency and maximal efficacy of agonist-induced responses while decreasing the dissociation of the agonist $N^6$-(4-amino-3-[$^{125}$I]iodobenzyl)-5'-N-methylcarboxamidoadenosine from human A3 adenosine receptors.

SUMMARY OF THE INVENTION

In accordance with the first aspect, the present invention provides the use of an $A_3$ adenosine receptor allosteric modulator ($A_3$RM) for the preparation of a pharmaceutical composition for the preparation of a pharmaceutical composition for the treatment of a condition which requires for said treatment modulation of $A_3$ adenosine receptor ($A_3$AR), wherein said $A_3$RM has the following general formula (I):

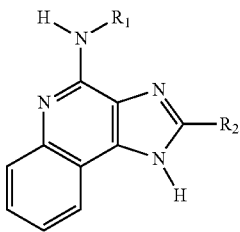

Formula I wherein:
$R_1$ represents an aryl or alkaryl being optionally substituted once or more at the aromatic ring with a substituent selected from $C_1$-$C_{10}$ alkyl, halo, $C_1$-$C_{10}$ alkanol, hydroxyl, $C_1$-$C_{10}$ acyl, $C_1$-$C_{10}$ alkoxyl, $C_1$-$C_{10}$-alkoxycarbony, $C_1$-$C_{10}$ alkoxylalkyl, $C_1$-$C_{10}$ thioalkoxy, $C_1$-$C_{10}$ alkylether, amino, hydrazido, $C_1$-$C_{10}$ alkylamino, pyridylthio, $C_2$-$C_{10}$ alkenyl; $C_2$-$C_{10}$ alkynyl, cyano, haloformyl, thio, $C_1$-$C_{10}$ alkylthio, acetoamido and sulfonic acid; or said substituents can form together a cycloalkyl or cycloalkenyl fused to said aryl, the cycloalkyl or cycloalkenyl optionally comprising one or more heteroatoms; provided that said aryl is not an unsubstituted phenyl group;

$R_2$ represents hydrogen or a substituent selected from $C_1$-$C_{10}$ alkyl, $C_2$-$C_{10}$ alkenyl, $C_2$-$C_{10}$ alkynyl, $C_4$-$C_{10}$ cycloalkyl, $C_4$-$C_{10}$ cycloalkenyl, $C_4$-$C_{10}$ heterocycloalkyl, $C_4$-$C_{10}$ heterocycloalkenyl, five to seven membered heterocyclic aromatic ring, $C_5$-$C_{15}$ bridged or fused cycloalkyl, bicyclic aromatic or heteroaromatic rings, $C_1$-$C_{10}$ alkylether, amino, hydrazido, $C_1$-$C_{10}$ alkylamino, $C_1$-$C_{10}$ alkoxy, $C_1$-$C_{10}$-alkoxycarbony, $C_1$-$C_{10}$ alkanol, $C_1$-$C_{10}$ acyl, $C_1$-$C_{10}$ thioalkoxy, pyridylthio, thio, and $C_1$-$C_{10}$ alkylthio, acetoamido, sulfonic acid each of said substituents being optionally substituted by at least one group selected from $C_1$-$C_{10}$ alkyl, halo, $C_1$-$C_{10}$ alkanol, hydroxyl, $C_1$-$C_{10}$ acyl, $C_1$-$C_{10}$ alkoxyl; $C_1$-$C_{10}$-alkoxycarbony, $C_1$-$C_{10}$ alkoxylalkyl, $C_1$-$C_{10}$ thioalkoxy; $C_1$-$C_{10}$ alkylether, amino, hydrazido, $C_1$-$C_{10}$ alkylamino, pyridylthio, $C_2$-$C_{10}$ alkenyl, $C_2$-$C_{10}$ alkynyl, cyano, haloformyl, isoindole-1,3-dione, thio, $C_1$-$C_{10}$ alkylthio, aryl, alkaryl, acetoamido and sulfonic acid, and any pharmaceutically acceptable salt thereof.

In accordance with a further aspect, there is also provide a method of modulating $A_3$ adenosine receptor ($A_3$AR) in a subject, the method comprises administering to said subject an amount of an $A_3$ adenosine receptor allosteric modulator ($A_3$RM), the amount being effective to modulate $A_3$AR activity, In accordance with yet a further aspect, there is provided a method of treating a subject for a condition which requires for said treatment modulation of $A_3$ adenosine receptor ($A_3$AR), the method comprises administering to said subject an amount of an $A_3$ adenosine receptor allosteric modulator ($A_3$RM) having the general formula as defined above, the amount of the $A_3$RM being effective to modulate $A_3$AR activity.

The invention also provides a pharmaceutical composition for the treatment of a condition which requires for said treatment modulation of $A_3$ adenosine receptor ($A_3$AR), the composition comprises as active ingredient an $A_3$ adenosine receptor allosteric modulator ($A_3$RM), having the general formula (I) as defined above.

A preferred composition in accordance with the invention is in the form suitable for oral administration.

The $A_3$RM is preferably utilized in accordance with the invention for enhancing the $A_3$AR.

The present invention also provides imidazoquinoline derivatives having the general formula I as defined above, for use as an $A_3$AR allosteric enhancer.

The invention also provides imidazoquinoline derivatives selected from:
N-(4-Methyl-phenyl)-2-cyclopentyl-1H-imidazo[4,5-c]quinolin-4-amine (31)
N-(4-Methoxy-phenyl)-2-cyclopentyl-1H-imidazo[4,5-c]quinolin-4-amine (32)
N-(3,4-Dichloro-phenyl)-2-cyclopentyl-1H-imidazo[4,5-c]quinolin-4-amine (33)
N-(4-Chloro-phenyl)-2-cyclopentyl-1H-imidazo[4,5-c]quinolin-4-amine (34)
N-(3-Methanol-phenyl)-2-cyclopentyl-1H-imidazo[4,5-c]quinolin-4-amine (35)
N-([3,4-c]Indan)-2-cyclopentyl-1H-imidazo[4,5-c]quinolin-4-amine (36)
N-(1H-indazol-6-yl)-2-cyclopentyl-1H-imidazo[4,5-c]quinolin-4-amine (37)
N-(4-Methoxy-benzyl)-2-cyclopentyl-1H-imidazo[4,5-c]quinolin-4-amine (38)
N-(1H-Indol-6-yl)-2-cyclopentyl-1H-imidazo[4,5-c]quinolin-4-amine (39)
N-(Benzyl)-2-cyclopentyl-1H-imidazo[4,5-c]quinolin-4-amine (40)
N-(Phenylethyl)-2-cyclopentyl-1H-imidazo[4,5-c]quinolin-4-amine (41)
N-(3,4-Dichloro-phenyl)-2-cycloheptyl-1H-imidazo[4,5-c]quinolin-4-amine (42)
N-(3,4-Dichloro-phenyl)-2-furyl-1H-imidazo[4,5-c]quinolin-4-amine (43)
N-(3,4-Dichloro-phenyl)-2-cyclobutyl-1H-imidazo[4,5-c]quinolin-4-amine (44)
N-(3,4-Dichloro-phenyl)-2-cyclohexyl-1H-imidazo[4,5-c]quinolin-4-amine (45)

N-(3,4-Dichloro-phenyl)-2-1H-imidazo[4,5-c]quinolin-4-amine (46)

N-(3,4-Dichloro-phenyl)-2-pentyl-1H-imidazo[4,5-c]quinolin-4-amine (47).

These imidazoquinoline derivatives are also some preferred $A_3RM$ in accordance with the invention. A specifically preferred imidazoquinoline derivative in accordance with the invention is N-(3,4-Dichloro-phenyl)-2-cyclohexyl-1H-imidazo[4,5-c]quinolin-4-amine (45)

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

Figure 1:
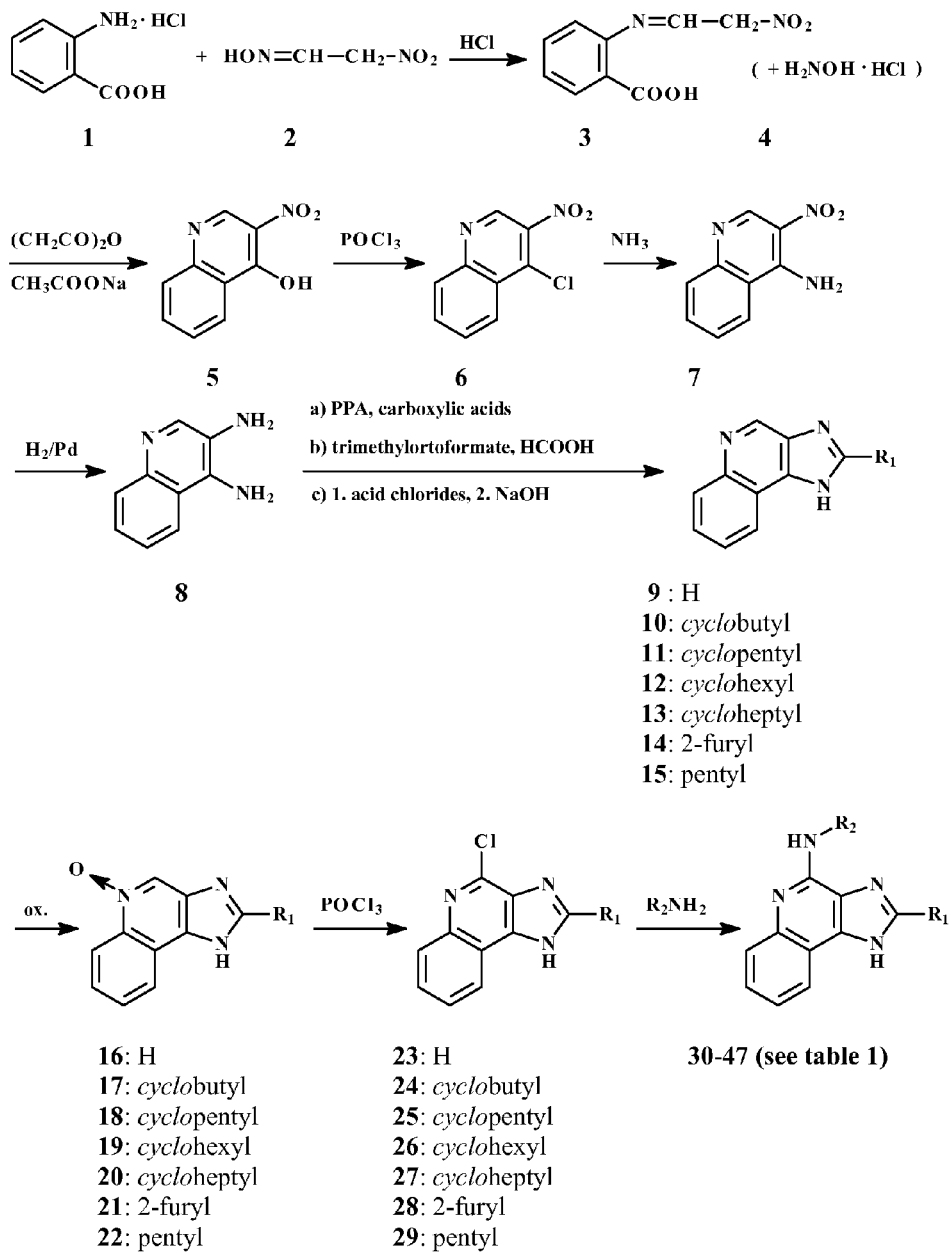
FIG. 1 is a scheme of the synthetic procedure of imidazoquinoline derivatives.

The present invention concerns allosteric modulation of the $A_3$ adenosine receptor ($A_3AR$) by the use of imidazoquinoline derivatives. It has been found that imidazoquinoline derivatives may effectively increase the efficacy of the receptor, upon binding to thereto.

As appreciated, while the invention is described in the following detailed description with reference to therapeutic methods comprising treatment with allosteric modulators of $A_3AR$, it is to be understood that also encompassed within the present invention are pharmaceutical compositions comprising $A_3$ adenosine receptor allosteric modulators, the uses of such $A_3$ adenosine receptor allosteric modulators, as well as some novel imidazoquinoline derivatives found to be specifically effective as allosteric modulators of the receptor.

As used herein, the term "allosteric modulation" which may be used interchangeably with the term "allosteric regulation" denotes the regulation or modulation of an enzyme, receptor or other protein by binding of an effector molecule at the protein's allosteric site which is different from the binding site of the endogenous ligand.

Effectors that enhance the protein's activity are referred to as "allosteric activators" or "allosteric enhancers", whereas those that decrease the protein's activation are called "allosteric inhibitors".

Further, as used in the specification and claims, the forms "a", "an" and "the" include singular as well as plural references unless the context clearly dictates otherwise. For example, the term "an imidazoquinoline derivative" denotes one or more compounds being the same or different chemical modifications of imidazoquinoline.

Further, as used herein, the term "comprising" is intended to mean that the methods and compositions of the invention may include the recited imidazoquinoline derivative but not excluding other substances. The term "consisting essentially of" is used to define methods and compositions that include the recited components but exclude other components that may have an essential significance on the biochemical response resulting from the binding of imidazoquinoline derivative to the receptor. For example, a composition consisting essentially of an imidazoquinoline derivative as the active ingredient and a pharmaceutically acceptable carrier will not include or include only insignificant amounts (amounts that will have an insignificant effect on the activity of the receptor) of other compounds capable of binding to the allosteric site or binding site of the receptor. "Consisting of" shall thus mean excluding more than trace elements of other components. Embodiments defined by each of these transition terms are within the scope of this invention.

Further, all numerical values, e.g. when referring the amounts or ranges of the components constituting the composition of the invention, are approximations which are varied (+) or (−) by up to 20%, at times by up to 10% of from the stated values. It is to be understood, even if not always explicitly stated that all numerical designations are preceded by the term "about".

Thus, in accordance with the first aspect, the present invention provides the use of an $A_3$ adenosine receptor allosteric modulator ($A_3RM$) for the preparation of a pharmaceutical composition for the preparation of a pharmaceutical composition for the treatment of a condition which requires for said treatment modulation of $A_3$ adenosine receptor ($A_3AR$), wherein said $A_3RM$ has the following general formula (I):

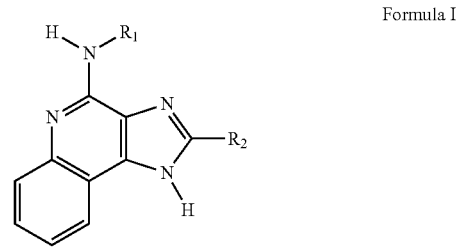

Formula I wherein:
$R_1$ represents an aryl or alkaryl being optionally substituted at the aromatic ring once or more with a substituent selected from $C_1$-$C_{10}$ alkyl, halo, $C_1$-$C_{10}$ alkanol, hydroxyl, $C_1$-$C_{10}$ acyl, $C_1$-$C_{10}$ alkoxyl; $C_1$-$C_{10}$-alkoxycarbony, $C_1$-$C_{10}$ alkoxylalkyl, $C_1$-$C_{10}$ thioalkoxy, $C_1$-$C_{10}$ alkylether, amino, hydrazido, $C_1$-$C_{10}$ alkylamino, pyridylthio, $C_2$-$C_{10}$ alkenyl, $C_2$-$C_{10}$ alkynyl, cyano, haloformyl, thio, $C_1$-$C_{10}$ alkylthio, acetoamido and sulfonic acid; or said substituents can form together a cycloalkyl or cycloalkenyl fused to said aryl, the cycloalkyl or cycloalkenyl optionally comprising one or more heteroatoms; provided that said aryl is not an unsubstituted phenyl group;

$R_2$ represents hydrogen or a substituent selected from $C_1$-$C_{10}$ alkyl, $C_2$-$C_{10}$ alkenyl, $C_2$-$C_{10}$ alkynyl, $C_4$-$C_{10}$ cycloalkyl, $C_4$-$C_{10}$ cycloalkenyl, $C_4$-$C_{10}$ heterocycloalkyl, $C_4$-$C_{10}$ heterocycloalkenyl, five to seven membered heterocyclic aromatic ring, $C_5$-$C_{15}$ fused cycloalkyl, bicyclic aromatic or heteroaromatic rings, $C_1$-$C_{10}$ alkylether, amino, hydrazido, $C_1$-$C_{10}$ alkylamino, $C_1$-$C_{10}$ alkoxy, $C_1$-$C_{10}$-alkoxycarbony, $C_1$-$C_{10}$ alkanol, $C_1$-$C_{10}$ acyl, $C_1$-$C_{10}$ thioalkoxy, pyridylthio, thio, and $C_1$-$C_{10}$ alkylthio, acetoamido and sulfonic acid, each of said substituents being optionally substituted by at least one group selected from $C_1$-$C_{10}$ alkyl, halo, $C_1$-$C_{10}$ alkanol, hydroxyl, $C_1$-$C_{10}$ acyl, $C_1$-$C_{10}$ alkoxyl; $C_1$-$C_{10}$-alkoxycarbony, $C_1$-$C_{10}$ alkoxylalkyl, $C_1$-$C_{10}$ thioalkoxy; $C_1$-$C_{10}$ alkylether, amino, hydrazido, $C_1$-$C_{10}$ alkylamino, pyridylthio, $C_2$-$C_{10}$ alkenyl, C₂-C₁₀ alkynyl, cyano, haloformyl, isoindole-1,3-dione, thio, C₁-C₁₀ alkylthio, aryl, alkaryl, acetoamido and sulfonic acid;

and any pharmaceutically acceptable salt thereof, for the preparation of a pharmaceutical composition for the treatment of a condition which requires for said treatment modulation of A₃ adenosine receptor (A₃AR).

Preferably, the composition is for enhancing A₃AR activity.

The term "alkyl" is used herein to refer to a linear or branched hydrocarbon chain having from 1 to 10 carbon atoms and more preferably 1 to 6 carbon atoms including, but not limited to, methyl, ethyl, n-propyl, isopropyl, n-butyl, t-butyl, n-heptyl, octyl and the like.

Similarly, the terms "alkenyl" and "alkynyl" denote a linear or branched hydrocarbon chain having, respectively, from 2 to 10, or from 3 to 10 carbon atoms and more preferably 2 to 6 or 3 to 6 carbon atoms, the alkenyl or alkynyl having at least one unsaturated bond.

The alkyl, alkenyl or alkynyl substituents may be substituted with a heteroatom containing group. Thus, it should be understood that while not explicitly stated, any of the alkyl modifications defined hereinabove and below, such as alkylthio, alkoxy, akanol, alkylamine etc, also include the corresponding alkenyl or alkynyl modifications, such as, akenylthio, akenyloxy, alkenol, alkenylamine, or respectively, akynylthio, alkynyloxy, alkynol, alkynylamine.

The term "aryl" denotes an unsaturated aromatic carbocyclic group of from 5 to 14 carbon atoms having a single ring (e.g., phenyl) or multiple condensed rings (e.g., naphthyl or anthryl). Preferred aryls include phenyl, indanyl, benzimidazole.

The term "alkaryl" refers to -alkylene-aryl groups preferably having from 1 to 10 carbon atoms in the alkylene moiety and from 6 to 14 carbon atoms in the aryl moiety. Such alkaryl groups are exemplified by benzyl, phenethyl and the like.

The term "Substituted aryl" refers to an aromatic moiety which is substituted with from 1 to 3 substituents as defined above. A variety of substituents are possible, as appreciated by those versed in the art. Nonetheless, some preferred substituents include, without being limited thereto, halogen, (substituted) amino, nitro, cyano, alkyl, alkoxy, acyloxy or alkanol, sulphonyl, sulphynyl.

The term "Halo" or "halogen" refers to fluoro, chloro, bromo and iodo, preferably to chloro.

The term "acyl" refers to the groups H—C(O)— as well as alkyl-C(O)—.

The term "alkanol" refers to the group —COH as well as alk-OH, "alk" denoting an alkylene, alkenylene or alkynylene chain.

The term "alkoxy" is used herein to mean —O-alkyl, including, but not limited to, methoxy, ethoxy, propoxy, isopropoxy, n-butoxy and the like.

The term "alkylthio" is used herein to mean —S-alkyl, including, but not limited to, methylthio, ethylthio, n-propylthio, isopropylthio, n-butylthio and the like.

The term "alkoxyalkyl" is used herein to mean -alkyl-O-alkyl, including, but not limited to, methoxymethyl, ethoxymethyl, n-propoxymethyl, isopropoxymethyl, n-butoxymethyl, isobutoxymethyl, t-butoxymethyl and the like.

The term "cycloalkyl" is used herein to mean cyclic hydrocarbon radicals including, but not limited to, cyclopropyl, cyclobutyl, cyclopentyl, cyclohexyl, cycloheptyl and the like.

The term "alkoxycarbonyl" is used herein to mean —C(O) O-alkyl, including, but not limited to, methoxycarbonyl, ethoxycarbonyl, propoxycarbonyl and the like.

The term "fused cycloalkyl" is used herein to mean any compound or substituent comprising at least two aliphatic rings which are connected at a single atom (to form a spirocyclic moiety), at two mutually bonded atoms or across a sequence of atoms (bridgehead). The fused rings may include any bicyclic, tricyclic as well as polycyclic moieties. Bicyclic substituents are preferred in accordance with this embodiment of the invention.

The term "haloform" as used herein is meant to encompass a —CX₃ radical, wherein X is any of the halogen atom, namely, Cl, Br, F and I. Specifically, the halogen atom is F.

The term "heterocycloalkyl" as used herein is meant to encompass a cyclic hydrocarbon having from 4 to 10 carbon atoms and at least one heteroatom selected from S, O, NH and NR, wherein R is a substituent as defined hereinabove. It should be noted that the heteroatom may be located at any position on the heterocycloalkyl ring. A non-limiting list of heterocycloaklyl moieties include: tetrahydro-pyranyl, tetrahydro-thiopyranyl, pyperidinyl and the like. The term "heterocycloalkenyl" as used herein is meant to encompass a cyclic hydrocarbon having from 4 to 10 carbon atoms, at least one double bond and at least one heteroatom selected from S, O, NH and NR, wherein R is a substituent as defined hereinabove. It should be noted that the heteroatom may be located at any position on the heterocycloalkylene ring.

The term "isoindole-1,3-dione" as used herein is meant to encompass a radical having the following formula:

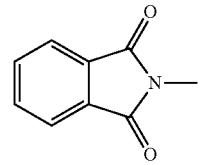

According to a more specific and preferred embodiment of the invention, the R₁ substituent in A₃RM has the following general formula (II):

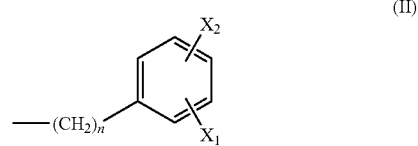

(II)

wherein n is 0 or an integer selected from 1-5; preferably, n is 0, 1 or 2; and

X₁ and X₂ which may be the same or different, are selected from hydrogen halogen, alkyl, alkanol or alkoxy, indanyl, pyrroline provided that when said n is 0, X₁ and X₂ are not hydrogen.

In yet a further preferred embodiment, R₁ in said A₃RM is a substituent having the above formula (II), wherein X₁ or X₂, which may be the same or different, are selected from hydrogen, chloro, methoxy, methanol or a substituent having the formulae (IIIa) or (IIIb):

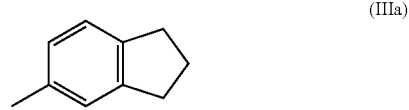

(IIIa)

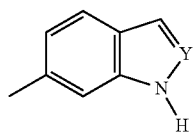

wherein Y is selected from N or CH.

In further embodiment $R_2$ in said $A_3RM$ is selected from H, $C_{1-10}$ alkyl, $C_{4-10}$ cycloalkyl, the alkyl chain may be a straight or branched or form a four to seven membered cycloalkyl ring.

In yet a further embodiment, $R_2$ in said $A_3RM$ is selected from a five to seven membered heterocyclic aromatic ring.

More preferred $R_2$ substituents are selected from H, n-pentyl, or a five membered heterocyclic aromatic ring having the following formula (IV):

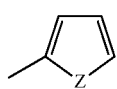

wherein Z is selected from O, S or NH, preferably O.

In accordance with another embodiment of the invention $R_2$ comprises fused rings, particularly so as to form bicyclic substituents. Non-limiting examples of bicyclic compounds which may be used to form the substituents in the context of the invention comprise bicyclo[2.2.1]heptane, bicyclo[4.1.0] heptane, bicyclo[4.1.0]heptan-3-carboxylic acid, bicyclo [3.1.0]hexan-3-carboxylic acid, bicyclo[4.1.0]heptan-2-carboxylic acid, bicyclo[3.1.0]hexan-2-carboxylic acid, and bicyclo[2.2.1]heptan-2-carboxylic acid.

In accordance with yet another embodiment, $R_2$ may be selected from 2-cyclohexene and 3-cyclohexene.

Specific imidazoquinoline derivatives in accordance with the invention are listed below:

N-(4-Methyl-phenyl)-2-cyclopentyl-1H-imidazo[4,5-c] quinolin-4-amine (31)

N-(4-Methoxy-phenyl)-2-cyclopentyl-1H-imidazo[4,5-c] quinolin-4-amine (32)

N-(3,4-Dichloro-phenyl)-2-cyclopentyl-1H-imidazo[4,5-c] quinolin-4-amine (33)

N-(4-Chloro-phenyl)-2-cyclopentyl-1H-imidazo[4,5-c] quinolin-4-amine (34)

N-(3-Methanol-phenyl)-2-cyclopentyl-1H-imidazo[4,5-c] quinolin-4-amine (35)

N-([3,4-c]Indan)-2-cyclopentyl-1H-imidazo[4,5-c]quinolin-4-amine (36)

N-(1H-indazol-6-yl)-2-cyclopentyl-1H-imidazo[4,5-c] quinolin-4-amine (37)

N-(4-Methoxy-benzyl)-2-cyclopentyl-1H-imidazo[4,5-c] quinolin-4-amine (38)

N-(1H-Indol-6-yl)-2-cyclopentyl-1H-imidazo[4,5-c]quinolin-4-amine (39)

N-(Benzyl)-2-cyclopentyl-1H-imidazo[4,5-c]quinolin-4-amine (40)

N-(Phenylethyl)-2-cyclopentyl-1H-imidazo[4,5-c]quinolin-4-amine (41)

N-(3,4-Dichloro-phenyl)-2-cycloheptyl-1H-imidazo[4,5-c] quinolin-4-amine (42)

N-(3,4-Dichloro-phenyl)-2-furyl-1H-imidazo[4,5-c]quinolin-4-amine (43)

N-(3,4-Dichloro-phenyl)-2-cyclobutyl-1H-imidazo[4,5-c] quinolin-4-amine (44)

N-(3,4-Dichloro-phenyl)-2-cyclohexyl-1H-imidazo[4,5-c] quinolin-4-amine (45)

N-(3,4-Dichloro-phenyl)-2-1H-imidazo[4,5-c]quinolin-4-amine (46)

N-(3,4-Dichloro-phenyl)-2-pentyl-1H-imidazo[4,5-c]quinolin-4-amine (47).

In general, the novel derivatives 31-47 were synthesized as shown in the scheme depicted in FIG. 1. Condensation of anthranilic acid hydrochloride (1) with methazonic acid (2) resulted in 2-β-nitroethylideneaminobenzoic acid (3), which was dehydrated in acetic anhydride in the presence of potassium acetate to give 3-nitro-4-hydroxyquinoline (5) [Bachman, G. B. et al. Quinoline Derivatives from 3-Nitro-4-hydroxyquinoline, *J. Am. Chem. Soc.*, 1947, 69, 365-371]. 3-Nitro-4-hydroxyquinoline (5) was treated with phosphorous oxychloride to afford 3-nitro-4-chloroquinoline (6). This was converted to 3-nitro-4-aminoquinoline (7) with ammonia, which was subsequently reduced by catalytic hydrogenation to 3,4-diaminoquinoline (8) with 10% palladium on charcoal as catalyst. The next step involved ring-closure, which was carried out in three different ways. For example, Compound 10 was prepared by ring closure of the appropriate carboxylic acid and 3,4-diaminoquinoline (8) in polyphosphoric acid [Young, R. C. et al. Purine Derivatives as Competitive Inhibitors of Human Erythrocyte Membrane Phosphatidylinositol 4-Kinase. *J. Med. Chem.* 1990, 33, 2073-2080]. Compound 14 was prepared by ring-closure of 2-furoyl chloride with 3,4-diaminoquinoline (8) [Scammells P. J. et al. Substituted 1,3-dipropylxanthines as irreversible antagonists of A1 adenosine receptors. J. Med. Chem. 1994, 37, 2704-2712]. Compound 9 was prepared by ring-closure of 3,4-diaminoquinoline (8) with formic acid in trimethylorthoformate. Oxidation with 3-chloroperoxybenzoic acid afforded 5-oxides 16-22, which subsequently could be converted with phosphorous oxychloride into the 4-chlorides 23-29. Finally, reaction with the appropriate amines afforded the desired compounds 30-47, respectively [Van Galen, P. J. M. et. al. 1-H-imidazo[4,5-c]quinolin-4-amines: Novel Non-Xanthine Adenosine Antagonists. *J. Med. Chem.* 1991, 34, 1202-1206].

It was surprisingly found that modifying the Van Galen procedure by using microwave irradiation (a short period of about 40 min max) in the last reaction step resulted in a significant reduction in the required reaction time as well as an easier and more straightforward purification of the end products. This was unexpected since microwave irradiation has not been thought to be relevant for this particular reaction.

It is noted that the above specific imidazoquinoline derivatives are novel per se and all have been shown to modulate the response obtained by their allosteric binding to $A_3AR$.

The imidazoquinoline derivatives of the invention where shown to have, on the one hand, reduced affinity, if any, to the orthosteric binding sites of the $A_1$ and $A_{2A}$, $A_{2B}$ adenosine receptors and reduced affinity to the orthosteric binding site of the $A_3$ adenosine receptor, and on the other hand, high affinity to the allosteric site of the $A_3$ adenosine receptor. This finding was unexpected in light of the non-specific affinity of known imidazoquinoline derivatives, such as N-phenyl-2-cyclopentyl-1H-imidazo[4,5-c]quinolin-4-amine (compound 30) to the orthosteric as well as allosteric binding sites of these receptors. The selective affinity of the derivatives disclosed herein is particularly evident with respect to compounds 33, 42, 44 and 45 in Tables 1 and 2.

As further shown in Table 2 hereinafter, the specific imidazoquinoline derivatives of the invention were shown to increase the activity of the $A_3AR$. Thus, in accordance with a further preferred embodiment of the invention modulation comprises enhancement of $A_3AR$ activity. In this context, the $A_3AM$ are considered as $A_3AR$ activators.

The term "enhancement" denotes the effect of the imidazoquinoline derivative on the receptor exhibited by an increase of at least 15% in the efficacy of the $A_3$ adenosine receptor by binding of the imidazoquinoline to the allosteric site of the receptor and/or by a decrease in dissociation rate of adenosine or an $A_3AR$ agonist to the orthosteric binding site.

Thus, in accordance with another of its aspects, the present invention provides a method of modulating $A_3$ adenosine receptor ($A_3AR$) in a subject, the method comprises administering to said subject an amount of an $A_3$ adenosine receptor allosteric modulator ($A_3RM$), the amount being effective to modulate $A_3AR$, wherein said $A_3RM$ has the general formula (I) as defined above.

The invention also provides a method of treating a subject for a condition which requires for said treatment modulation of $A_3$ adenosine receptor ($A_3AR$), the method comprises administering to said subject an amount of the $A_3RM$ as defined above, the amount being effective to modulate $A_3AR$ activity.

The term treatment "treatment" as used herein refers to the administering of a therapeutic amount of the imidazoquinoline derivative as defined herein, alone or in combination with a ligand to the $A_3AR$ orthosteric binding site which is effective to achieve a therapeutic effect, the therapeutic effect being selected from one or more of the following: amelioration of undesired symptoms associated with a disease, prevention of the manifestation of such symptoms before they occur, slowing down a progression of the disease, slowing down any deterioration of symptoms, enhancement of onset of a remission period, slowing down of any irreversible damage caused in a progressive chronic stage of the disease, delaying of the onset of said progressive stage, lessening of the severity or cure of a disease, improving survival rate or more rapid recovery from a disease, preventing the disease form occurring or a combination of two or more of the above.

A variety of conditions may be treated by the modulation of the $A_3AR$ depending on the specific effect the imidazoquinoline has on the receptor.

When said modulation comprises inhibition of or decrease in efficacy of the receptor, the condition may be any condition which may also be treated by the binding of an A3 adenosine receptor antagonist. Such conditions comprise, without being limited thereto, certain malignancies, certain immuno-compromised afflictions, and high intraocular pressure.

When said modulation comprises enhancement or increase in efficacy of the receptor, the condition may be any condition which may also be treated by the binding of an $A_3$ adenosine receptor agonist. Such conditions comprise, without being limited thereto, hyperproliferative disorders, and in particular all types of solid tumors; skin proliferative diseases (e.g. psoriasis); a variety of benign hyperplasic disorders; inflammatory diseases; ischemic conditions, such as myocardial or renal ischemia.

The term "solid tumors" refers to carcinomas, sarcomas, adenomas, and cancers of neuronal origin and if fact to any type of cancer which does not originate from the hematopoeitic cells and in particular concerns: carcinoma, sarcoma, adenoma, hepatocellular carcinoma, hepatocellularcarcinoma, hepatoblastoma, rhabdomyosarcoma, esophageal carcinoma, thyroid carcinoma, ganglioblastoma, fibrosarcoma, myxosarcoma, liposarcoma, cohndrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small lung carcinoma, bladder carcinoma, epithelial carcinoma, glioma, astrocyoma, medulloblastoma, craniopharyngioma, ependynoma, pinealoma, retinoblastoma, multiple myeloma, rectal carcinoma, thyroid cancer, head and neck cancer, brain cancer, cancer of the peripherial nervous system, cancer of the central nervous system, neuroblastoma, cancer of the endometrium, as well as metastasis of all the above. It has been shown in accordance with the invention that increased expression of $A_3AR$ can be found not only in the primary tumor site but also in metastases thereof.

Benign hyperplasic disorders include, without being limited thereto, benign prostate hyperplasia (BPH), non-tumorigenic polyps in the digestive tract, in the uterus and others.

Inflammatory diseases include, without being limited thereto, rheumatoid arthritis, Crohn's disease, multiple sclerosis and others.

It should be appreciated that the method of the invention may also comprise the combined administration of the $A_3RM$ in combination with a ligand to the orthosteric binding site. When modulation involves enhancement of the receptor, the $A_3RM$ may be administered in combination with adenosine or an $A_3AR$ agonist.

The term "combination" includes a schedule of treatment that involves administration of at least the $A_3RM$ and the ligand to the orthosteric site. The schedule of treatment may comprise simultaneous or co-administration of the two active principles, or with an interval between administrations.

According to a preferred embodiment, the $A_3RM$ is administered to the subject orally, although other administration routes are applicable, including parenteral (intravenous, intramuscular, intra-arterial, subcutaneous, intranasal, via the lungs (inhalation)).

The $A_3RM$ is preferably used and administered in combination with a physiologically acceptable carrier to form a pharmaceutical composition, the latter also forming part of the invention.

The term "physiologically acceptable excipient" denotes any excipient that is useful in preparing a pharmaceutical composition or formulation that is generally safe, non-toxic and neither biologically nor otherwise undesirable, and includes a excipient that is acceptable for veterinary use as well as human pharmaceutical use.

In making the compositions of this invention, the imidazoquinoline derivative is usually mixed with the excipient, diluted by an excipient or enclosed within a carrier which can be in the form of a capsule, sachet, paper or other container. When the excipient serves as a diluent, it can be a solid, semi-solid, or liquid material, which acts as a vehicle, carrier or medium for the imidazoquinoline derivative. Thus, the compositions can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders.

The effective amount of imidazoquinoline derivative in the pharmaceutical composition and unit dosage form thereof may be varied or adjusted widely depending upon the particular application, the manner or introduction, the potency of the particular compound, and the desired concentration. The effective amount is typically determined in appropriately designed clinical trials (dose range studies) and the person versed in the art will know how to properly conduct such trials in order to determine the effective amount. As generally known, an effective amount depends on a variety of factors including the affinity of the imidazoquinoline derivative to the allosteric binding site, its distribution profile within the body, a variety of pharmacological parameters such as half life in the body, on undesired side effects, if any, on factors such as age and gender, etc.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. The amount of therapeutically active compound in such a unit dosage form may vary from about 0.5 mg to 500 mg.

In this case, the composition of the invention will typically be administered over an extended period of time in a single daily dose, in several doses a day, as a single dose and in several days, etc. The treatment period will generally have a length proportional to the length of the disease process and the specific imidazoquinoline derivative effectiveness and the patient species being treated.

Some Exemplary Embodiments
Materials and Methods
Instruments and Analysis

Microwave-assisted chemistry was performed on an Emrys™ Optimizer with Emrys™ Optimizer software. For the reactions round-bottom vials with a volume of 2-5 mL were used.

$^1$H-NMR spectra were measured at 200 MHz with a Bruker AC 200 or Bruker DMX 600 spectrometer. $^{13}$C-NMR spectra were measured at 50 or 150 MHz. Chemical shifts for $^1$H and $^{13}$C are given in ppm (δ) relative to tetramethylsilane (TMS) as internal standard, coupling constants are given in Hz. Melting points were determined with a Büchi capillary melting point apparatus and are uncorrected. Combustion analyses of new target compounds were performed by the analytical department of the Gorlaeus Laboratories, Leiden University (The Netherlands) and are within 0.4% of theoretical values unless otherwise specified.

Chemical Synthesis

2-β-Nitroethylideaminobenzoic acid (compound 3)

Compound 3 was prepared as described elsewhere [Bachman, G. B. et al. Quinoline Derivatives from 3-Nitro-4-hydroxyquinoline, J. Am. Chem. Soc., 1947, 69, 365-371]. In brief, a solution of NaOH (13.4 g) in water (26.8 ml) was cooled and stirred. Nitromethane (6.7 g, 5.9 ml, 110 mmol) was added dropwise, keeping the temperature at 25-30° C. The mixture was then warmed to 40° C. and again cooled and stirred while another portion of nitromethane (6.7 g, 5.9 ml, 110 mmol) was added slowly at 40-45° C. This temperature was maintained until all solid was dissolved and a clear red solution was obtained. The solution was then heated to 50-55° C. for two to five minutes and finally cooled to 30° C., poured on chipped ice (30 g) and acidified with concentrated HCl (30 ml). The resultant solution of methazonic acid 2 was immediately added to a solution of anthranilic acid 1 (13.7 g, 100 mmol) and concentrated HCl (9.2 ml) in water (200 ml). Yellow precipitate formed, which was left to stand at room temperature for 12-18 h. The precipitate was filtered off and washed with water. The cake was sliced into thin flakes and dried. Yield: 18.40 g (89%). Mp.: 196°-197° C. $^1$H NMR (DMSO-d$_6$): δ 6.76 (d, 2H, J=6.6 Hz, CH$_2$); 7.24 (t, 1H, J=6.6 Hz, N=CH); 7.54-7.82 (m, 2H, Ar); 8.02-8.12 (m, 2H, Ar); 12.09 (s, 1H, COOH).

3-Nitro-4-hydroxyquinoline (compound 5)

Compound 5 was prepared as described elsewhere [Bachman, G. B. et al. Quinoline Derivatives from 3-Nitro-4-hydroxyquinoline, J. Am. Chem. Soc., 1947, 69, 365-371]. In brief, a mixture of 2-β-nitroethylideaminobenzoic acid 3 (10.4 g, 50 mmol) and technical acetic anhydride (50 ml) was placed in a 3-necked flask of at least 100 mL capacity fitted with thermometer, magnetic stirrer and reflux condenser. It was stirred and heated to 100-105° C. until a clear solution was obtained. Heating was then discontinued and anhydrous potassium acetate (5.0 g, 51 mmol) was added rapidly with stirring. The temperature rose spontaneously to 134-138° C. When it began to fall (five to ten minutes) external heating was applied and the mixture was refluxed for fifteen minutes with vigorous stirring, then allowed to cool slowly to room temperature. The product filtered off and washed with glacial acetic acid until the washings were colorless. Then suspended in water (50 ml) and dried in vacuum at 80° C. Yield: 6.93 g (49%). Mp.: >300° C. $^1$H NMR (DMSO-d$_6$): δ 7.54 (t, 1H, J=7.3 Hz, Ar); 7.76-7.86 (m, 2H, Ar); 8.27 (d, 1H, J=8.0 Hz, Ar); 9.21 (s, 1H, Ar).

3-Nitro-4-chloroquinoline (compound 6)

Compound 6 was prepared as described elsewhere [Van Galen, P. J. M. et. al. 1-H-imidazo[4,5-c]quinolin-4-amines: Novel Non-Xanthine Adenosine Antagonists. J. Med. Chem. 1991, 34, 1202-1206]. In brief, 3-Nitro-4-hydroxyquinoline 5 (5.7 g, 30 mmol) was added to phosphorus oxychloride (70.0 g, 41.2 ml, 450 mmol) with stirring. The mixture was refluxed for 30 minutes. After cooling the solvent was poured over crushed ice while stirring. After 1 hour the solid that was formed was filtered off, washed with cold water and dissolved in ethyl acetate. The solution was extracted with ice-cold NaOH (1 M) till pH=8-9 and dried over MgSO$_4$. The solvent was evaporated and the residue was dried. Yield: 5.05 g (81%). Mp.: 118°-119° C. $^1$H NMR (DMSO-d$_6$): δ 7.94-8.11 (m, 2H, Ar); 8.25 (d, 1H, J=8.0 Hz, Ar); 8.47 (d, 1H, J=9.5 Hz, Ar); 9.42 (s, 1H, Ar).

3-Nitro-4-aminoquinoline (compound 7)

Compound 7 was prepared as described elsewhere [Van Galen, P. J. M. et. al. (1991) ibid.]. In brief, ammonia gas was passed, while stirring, through a solution of 3-nitro-4-chloroquinoline 6 (7.0 g, 30 mmol) in toluene (95 ml) and propanol (15 ml) till the product was formed. During the course of the reaction, the temperature was gradually raised till 70° C. After cooling, the solid was separated by filtration and washed successfully with toluene/2-propanol (70:30), ether and cold water until Cl$^-$ could no longer be detected. The solid was filtered off and dried at 80° C. Yield: 6.1 g (95%). Mp.: 255-257° C. $^1$H NMR (DMSO-d$_6$): δ 7.50-7.66 (m, 1H, Ar); 7.81-7.92 (m, 2H, Ar); 8.59 (d, 1H, J=8.0 Hz, Ar); 9.03 (broad s, 2H, NH$_2$); 9.18 (s, 1H, Ar)

3,4-Diaminoquinoline (compound 8)

Compound 8 was prepared as described elsewhere [Van Galen, P. J. M. et. al. (1991) ibid.]. In brief, to a mixture of 3-nitro-4-aminoquinoline 7 (3.2 g, 20 mmol) in absolute ethanol (60 ml) was added 10% palladium on charcoal (0.17 g).

The mixture was hydrogenated under 2.5-3.5 atm pressure till the product was formed and subsequently filtered over Hyflo. The filtrate was evaporated and the residue was gradually solidified and dried in vacuum. Yield: 2.66 g (98%). Mp.: 183-185° C. MS (ESI) m/z 161.0 (M+1)$^+$. $^1$H NMR (DMSO-d$_6$): δ 4.73 (broad s, 2H, NH$_2$); 5.88 (s, 2H, NH$_2$); 7.16-7.37 (m, 2H, Ar); 7.64-7.70 (m, 1H, Ar); 7.98-8.03 (m, 1H, Ar); 8.22 (s, 1H, Ar).

General procedure of 1H-Imidazo[4,5-c]quinolines (Compounds 9-13)

1H-Imidazo[4,5-c]quinolines were prepared as described elsewhere [Young, R. C. et al. Purine Derivatives as Competitive Inhibitors of Human Erythrocyte Membrane Phosphatidylinositol 4-Kinase. *J. Med. Chem.* 1990, 33, 2073-2080]. In brief, polyphosphoric acid (1.3 ml/mmol) was added to 3,4-diaminoquinoline 8 and the appropriate carboxylic acid (1.2 eq.). The mixture was stirred at 100° C. for 5 hours. Then cooled to 0° C. and NH$_4$OH was added slowly till pH=8-9. The mixture was extracted with ethyl acetate (3 times 15 ml), then washed with water, brine and again water and dried over MgSO$_4$. The solvent was evaporated and the residue was dried.

1H-Imidazo[4,5-c]quinoline (compound 9)

Compound 9 was prepared as described elsewhere [Van Galen, P. J. M. et. al. (1991) ibid.]. In brief, compound 8 (1.4 g, 8.71 mmol) was heated under stirring with trimethyl orthoformate (23.8 ml). To a clear solution was cautiously added formic acid (0.45 ml) whereupon solid precipitated. The mixture was refluxed for 1 hour. After cooling to 40° C., ether (3.1 ml) and absolute ethanol (0.36 ml) were added and the mixture was cooled on ice for 1 hour. The solid that was formed was filtered off, washed with ether and subsequently with ethyl acetate and dried. Yield: 0.44 g (81%). Mp.: 263-265° C. $^1$H NMR (DMSO-d$_6$): δ 7.67-7.72 (m, 2H, Ar); 8.18 (s, 1H, Ar); 8.29-8.34 (m, 1H, Ar); 8.61-8.65 (m, 1H, Ar); 8.93 (s, 1H, Ar).

2-Cyclobutyl-1H-Imidazo[4,5-c]quinoline (compound 10)

Scale: 6.2 mmol Eluent for column chromatography was ethyl acetate:petroleum ether=1:1. Yield: 0.88 g (63%). Mp.: 191-192° C. MS (ESI) m/z 223.6 (M+1)$^+$. $^1$H NMR (CD$_3$OD): δ 1.95-2.32 (m, 2H, CH$_2$); 2.44-2.66 (m, 4H, 2CH$_2$); 3.82-4.01 (m, 1H, CH); 7.58-7.71 (m, 2H, Ar); 8.01-8.11 (m, 1H, Ar); 8.32-8.38 (m, 1H, Ar); 9.01 (s, 1H, Ar).

2-Cyclopentyl-1H-Imidazo[4,5-c]quinoline (compound II)

Scale: 4.0 mmol Eluent for column chromatography was 5% methanol in dichloromethane. Yield: 0.77 g (81%). Mp.: 192° C. $^1$H NMR (CDCl$_3$): δ 1.70-1.88 (m, 6H, 3CH$_2$); 2.03-2.22 (m, 2H, CH$_2$); 3.39-3.56 (m, 1H, CH); 7.27 (s, 1H, Ar); 7.53-7.66 (m, 2H, Ar); 8.21 (d, 2H, J=8.0 Hz, Ar); 9.18 (s, 1H, NH).

2-Cyclohexyl-1H-Imidazo[4,5-c]quinoline (compound 12)

Scale: 6.3 mmol Eluent for column chromatography was 1-5% methanol in dichloromethane. Yield: 0.60 g (38%). Mp.: 205-206° C. MS (ESI) m/z 251.7 (M+1)$^+$. $^1$H NMR (CDCl$_3$): δ 1.12-1.39 (m, 4H, 2CH$_2$); 1.66-1.77 (m, 4H, 2CH$_2$); 2.16-2.21 (m, 2H, CH$_2$); 3.01-3.13 (m, 1H, CH); 7.41-7.60 (m, 2H, Ar); 8.19 (d, 1H, J=8.8 Hz, Ar); 8.31 (d, 1H, J=8.0 Hz, Ar); 9.16 (s, 1H, Ar).

2-Cycloheptyl-1H-Imidazo[4,5-c]quinoline (compound 13)

Scale: 6.3 mmol Eluent for column chromatography was 1-5% methanol in dichloromethane. Yield: 0.45 g (27%). Mp.: 225-226° C. MS (ESI) m/z 266.3 (M+1)$^+$.
$^1$H NMR (CDCl$_3$): δ 1.25-1.24 (m, 12H, 6CH$_2$); 3.20-3.32 (m, 1H, CH); 7.42-7.62 (m, 2H, Ar); 8.20 (d, 1H, J=8.0 Hz, Ar); 8.33 (d, 1H, J=8.0 Hz, Ar); 9.19 (s, 1H, Ar).

2-Furyl-1H-Imidazo[4,5-c]quinoline (compound 14)

2-Furoyl chloride (1.1 g, 0.8 ml, 8.1 mmol) in dry dichloromethane (15 ml) was added dropwise to a solution of to 3,4-diaminoquinoline 8 (1.0 g, 6.0 mmol) in dry pyridine (6.2 ml) under nitrogen. The solution was stirred for 2 hours at room temperature. Water (15 ml) was added to quench the reaction and the solvent was evaporated under reduced pressure to afford an orange solid. This crude solid in 2N NaOH (15 ml) was refluxed for 2 hours. After cooling on ice the pH was adjusted to 7 using concentrated HCl. The solid that precipitated was filtered off and washed with water and ether. Then extracted with ethyl acetate (3 times 15 ml) and washed with water (3 time 15 ml) and dried over MgSO$_4$. The solvent was evaporated and the residue was dried. Eluent for column chromatography was 1-5% methanol in dichloromethane. Yield: 0.62 g (44%). Mp.: 236-238° C. $^1$H NMR (DMSO-d$_6$): δ 6.74 (s, 1H, Ar); 7.35 (d, 1H, J=3.7 Hz, Ar); 7.69-7.73 (m, 2H, Ar); 7.83 (s, 1H, Ar); 8.09 (s, 1H, Ar); 8.46 (s, 1H, Ar); 9.09 (s, 1H, Ar). $^{13}$C NMR (DMSO-d$_6$): δ 111.4, 112.6, 120.7, 121.8, 126.5, 127.2, 129.5, 138.2, 143.6, 144.3, 145.1, 147.2, 155.4.

2-Pentyl-1H-Imidazo[4,5-c]quinoline (compound 15)

Prepared as described for the furyl compound (14) using hexanoyl chloride (1.75 g, 13 mmol). Eluent for column chromatography was ethyl acetate:petroleum ether 1:4 to 4:1. Yield: 0.85 g (41%): mp 142-143° C. $^1$H NMR (DMSO-d$_6$): δ 0.91 (t, 3H, J=6, CH$_3$), 1.37-1.39 (m, 4H, 2×CH$_2$), 1.83-1.91 (m, 2H, CH$_2$), 1.93-2.30 (t, 2H, J=8, CH$_2$), 7.64-7.69 (m, 2H, Ar); 8.08-8.13 (m, 1H, Ar); 8.28-8.42 (m, 1H, Ar); 9.12 (s, 1H, Ar).

General procedure of 2-substituted 1H-Imidazo[4,5-c]quinolin-5-oxide (compounds 16-22)

Staring material (9-15) was almost completely dissolved (with heating) in chloroform (2.5 ml/mmol), dichloromethane (2.5 ml/mmol) and methanol (0.25 ml/mmol). 3-Chloroperoxybenzoic acid (2.5 eq.) was added and the solution was reflux. After 30 minutes Na$_2$CO$_3$ (0.04 g/mmol) was added and the mixture was refluxed for one more hour. The reaction mixture was cooled on an ice-bath and the solvent was evaporated. Column chromatography was needed for purification and removal of 3-chloroperoxybenzoic acid.

1H-Imidazo[4,5-c]quinolin-5-oxide (compound 16)

Scale: 8.3 mmol Eluent for column chromatography was 2% methanol in dichloromethane. Yield: 0.55 g (36%). Mp.:

290-295° C. ¹H NMR (CD₃OD): δ 7.41-7.61 (m, 1H, Ar); 7.87-7.96 (m, 2H, Ar); 8.45-8.53 (m, 1H, Ar); 8.75-8.80 (m, 1H, Ar); 9.16 (s, 1H, Ar).

2-Cyclobutyl-1H-imidazo[4,5-c]quinolin-5-oxide (compound 17)

Scale: 1.8 mmol Eluent for column chromatography was 2% (increased to 6%) methanol in dichloromethane. Yield: 0.18 g (42%). Mp.: 123-130° C. ¹H NMR (DMSO-d₆): δ 1.95-2.22 (m, 2H, CH₂); 2.38-2.59 (m, 4H, 2CH₂); 3.41-3.93 (m, 1H, CH); 7.72-7.93 (m, 2H, Ar); 8.39-8.41 (m, 1H, Ar); 8.65-8.99 (m, 1H, Ar); 11.52 (s, 1H, Ar).

2-Cyclopentyl-1H-imidazo[4,5-c]quinolin-5-oxide (compound 18)

Scale: 0.8 mmol Eluent for column chromatography was 5% methanol in dichloromethane. Yield: 0.19 g (95%). Mp.: 155-157° C. ¹H NMR (CD₃OD): δ 1.74-2.13 (m, 6H, 3CH₂); 2.18-2.39 (m, 2H, CH₂); 3.38-3.54 (m, 1H, CH); 7.29-7.42 (m, 2H, Ar); 7.83-7.92 (m, 2H, Ar); 9.03 (s, 1H, Ar).

2-Cyclohexyl-1H-imidazo[4,5-c]quinolin-5-oxide (compound 19)

Scale: 2.4 mmol Eluent for column chromatography was 5-10% methanol in dichloromethane. Yield: 0.59 g (92%). Mp.: 160-165° C. ¹H NMR (CD₃OD): δ 1.17-2.19 (m, 10H, 5CH₂); 2.97-3.12 (m, 1H, CH); 7.79-7.93 (m, 2H, Ar); 8.42-8.46 (m, 1H, Ar); 8.69-8.77 (m, 1H, Ar); 9.03 (s, 1H, Ar). ¹³C NMR (CD₃OD): δ 26.6, 26.8, 32.5, 39.7, 120.8, 123.1, 128.6, 129.9, 130.1, 130.3, 132.5, 138.0, 142.6, 164.1, 166.0, 170.9, 173.8.

2-Cycloheptyl-1H-imidazo[4,5-c]quinolin-5-oxide (compound 20)

Scale: 2.0 mmol Eluent for column chromatography was 3-8% methanol in dichloromethane. Yield: 0.22 g (39%). Mp.: 115-120° C. ¹H NMR (CD₃OD): δ 1.67-2.11 (m, 12H, 6CH₂); 3.05-3.31 (m, 1H, CH); 7.78-7.90 (m, 2H, Ar); 8.28-8.48 (m, 1H, Ar); 8.62-8.73 (m, 1H, Ar); 9.00 (s, 1H, Ar). ¹³C NMR (CD₃OD): δ 25.0, 26.4, 32.1, 39.2, 117.4, 118.2, 120.6, 126.2, 127.4, 127.8, 128.2, 130.0, 130.6, 132.3, 132.6, 135.2, 162.7, 166.5.

2-Furyl-1H-imidazo[4,5-c]quinolin-5-oxide (compound 21)

Scale: 2.2 mmol Eluent for column chromatography was 1-10% methanol in dichloromethane. Yield: 0.36 g (66%). Mp.: >280° C. ¹H NMR (CD₃OD): δ 6.74-6.77 (m, 1H, Ar); 7.37-7.47 (m, 2H, Ar); 7.87-7.96 (m, 2H, Ar); 8.55-8.60 (m, 1H, Ar); 8.74-8.79 (m, 1H, Ar); 9.07 (s, 1H, Ar).

2-Pentyl-1H-imidazo[4,5-c]quinolin-5-oxide (compound 22)

Scale: 3.34 mmol Eluent for column chromatography was 1-5% methanol in dichloromethane. Yield: 0.12 g (14%): ¹H NMR (CD₃OD): δ 0.88-0.94 (t, 3H, CH₃, J=6 Hz); 1.26-1.39 (m, 4H, 2×CH₂); 1.81-1.88 (m, 2H, CH₂); 2.88-2.95 (t, 2H, CH₂, J=8 Hz); 7.44-7.58 (m, 2H, Ar); 7.90-8.09 (m, 2H, Ar); 9.03 (s, 1H, Ar).

General procedure of 4-chloro-1H-imidazo[4,5-c]quinoline (compounds 23-29)

A mixture of toluene (0.45 ml/mmol) and dimethylformamide (0.90 ml/mmol) was cooled in an ice-bath and phosphorus oxychloride (2.6 eq.) was added. After 10 minutes the appropriate 1H-imidazo[4,5-c]quinolin-5-oxide was added and the solution was stirred at room temperature for 10 minutes. Subsequently the solution was heated to 100° C. on a steam bath for 30 minutes. Upon cooling, the solvent was evaporated and the resulting syrup was poured over crushed ice while stirring. The mixture was then warmed to room temperature and carefully adjusted to pH 6-7 with solid NaHCO₃. After 2 hours, the solid that was formed was filtered off, washed with water and diisopropylether and subsequently dried.

4-Chloro-1H-imidazo[4,5-c]quinoline (compound 23)

Scale: 3.5 mmol Eluent for column chromatography was 2% methanol in dichloromethane. Yield: 0.31 g (44%). Mp.: 257-258° C. MS (ESI) m/z 203.8 (M+1)⁺, 206.0 (M+3)⁺. ¹H NMR (CDCl₃): δ 8.46-8.56 (m, 2H, Ar); 8.82-8.87 (m, 1H, Ar); 9.14-9.19 (m, 1H, Ar); 9.35 (s, 1H, Ar); 10.16 (broad s, 1H, NH).

4-Chloro-2-cyclobutyl-1H-imidazo[4,5-c]quinoline (compound 24)

Scale: 0.6 mmol Yield: 0.16 g (99%). Mp.: 142-145° C. ¹H NMR (CDCl₃): δ 2.06-2.24 (m, 2H, CH₂); 2.52-2.66 (m, 4H, 2CH₂); 3.87-4.00 (m, 1H, CH); 7.56-7.68 (m, 2H, Ar); 8.02-8.06 (m, 1H, Ar); 8.30-8.32 (m, 1H, Ar).

4-Chloro-2-cyclopentyl-1H-imidazo[4,5-c]quinoline (compound 25)

Scale: 12.7 mmol Yield: 2.65 g (75%). Mp.: >265° C. ¹H NMR (CD₃OD): δ 1.81-2.22 (m, 6H, 3CH₂); 2.25-2.31 (m, 2H, CH₂); 3.40-3.51 (m, 1H, CH); 7.63-7.74 (m, 2H, Ar); 8.00-8.03 (m, 1H, Ar); 8.33-8.38 (m, 1H, Ar).

4-Chloro-2-cyclohexyl-1H-imidazo[4,5-c]quinoline (compound 26)

Scale: 2.2 mmol Yield: 0.65 g (97%). Mp.: 245-250° C. MS (ESI) m/z 285.9 (M+1)⁺, 288.0 (M+3)⁺. ¹H NMR (CD₃OD): δ 1.37-2.17 (m, 10H, 5CH₂); 3.03-3.18 (m, 1H, CH); 7.68-7.71 (m, 2H, Ar); 8.00-8.08 (m, 1H, Ar); 8.32-8.40 (m, 1H, Ar).

4-Chloro-2-cycloheptyl-1H-imidazo[4,5-c]quinoline (compound 27)

Scale: 0.8 mmol Yield: 0.38 g (86%). Mp.: 195-200° C. MS (ESI) m/z 299.9 (M+1)⁺, 301.7 (M+3)⁺. ¹H NMR (CD₃OD): δ 1.73-2.13 (m, 12H, 6CH₂); 3.21-3.40 (m, 1H, CH); 7.63-7.79 (m, 2H, Ar); 7.97-8.05 (m, 1H, Ar); 8.29-8.38 (m, 1H, Ar).

4-Chloro-2-furyl-1H-imidazo[4,5-c]quinoline (compound 28)

Scale: 1.4 mmol Eluent for column chromatography was petroleum ether:ethyl acetate: =75:25. Yield: 0.1 g (26%).

Mp.: 235-238° C. MS (ESI) m/z 269.8 (M+1)⁺, 272.1 (M+3)⁺. ¹H NMR (CD₃OD): 6.72-6.75 (m, 1H, Ar); 7.40-7.43 (m, 1H, Ar); 7.63-7.75 (m, 2H, Ar); 7.83-7.88 (m, 1H, Ar); 7.98-8.01 (m, 1H, Ar); 8.36-8.40 (m, 1H, Ar).

4-Chloro-2-pentyl-1H-imidazo[4,5-c]quinoline (compound 29)

Scale: 0.45 mmol Yield: 0.052 g (41%): mp 236-237° C.; MS (ESI) m/z 273.9 (M+1)⁺, ¹H NMR (CDCl₃): δ 0.65-0.72 (t, 3H, CH₃, J=6 Hz); 1.14-1.21 (m, 4H, 2×☐CH₂); 1.61-1.72 (m, 2H, CH₂); 2.76-2.84 (t, 2H, CH₂, J=8 Hz); 7.33-7.47 (m, 2H, Ar); 7.76-7.80 (m, 1H, Ar); 7.95-8.15 (m, 1H, Ar).

General procedure of N-substituted 1H-imidazo[4,5-c]quinolin-4-amines (compounds 30-47)

These compounds were prepared by means of microwave-assisted chemistry. Absolute ethanol (2.5-3.0 ml) was added to the appropriate 4-chloro-1H-imidazo[4,5-c]quinoline and appropriate aniline (2-3 eq.). Conditions: pre stirring 60 seconds, temperature 120° C., time 2400 seconds, normal sample absorption, fixed hold time. After the reaction was completed the solvent was evaporated and the remaining product was purified by column chromatography and recrystallized.

N-Phenyl-2-cyclopentyl-1H-imidazo[4,5-c]quinolin-4-amine (compound 30)

Compound 30 was prepared as described elsewhere [Van Galen P. J. M. et al. (1991) ibid.].
Scale: 0.8 mmol Eluent for column chromatography was 2.5-10% methanol in dichloromethane. Yield: 40 mg (15%). The product was recrystallized from methanol. Mp.: 155-157° C. MS (ESI) m/z 328.9 (M+1)⁺. ¹H NMR (CDCl₃): δ 1.80-2.27 (m, 8H, 4CH₂); 3.31-3.55 (m, 1H, CH); 7.00-7.09 (m, 1H, Ar); 7.15-7.29 (m, 4H, Ar); 7.49-7.56 (m, 1H, Ar); 7.78 (d, 1H, J=6.6 Hz, Ar); 7.96-8.09 (m, 2H, Ar). ¹³C NMR 750 MHz (CDCl₃): δ 24.9, 31.7, 38.9, 114.7, 117.9, 118.1, 118.3, 119.2, 119.8, 120.9, 121.9, 123.6, 124.1, 126.2, 126.4, 126.5, 126.7, 128.1, 128.2, 128.9, 133.5, 140.5, 143.3, 146.6, 156.3, 159.1. Anal. (C₂₁H₂₀N₄.0.7H₂O) C, H, N.

N-(4-Methyl-phenyl)-2-cyclopentyl-1H-imidazo[4,5-c]quinolin-4-amine (compound 31)

Scale: 0.7 mmol Eluent for column chromatography was 1% methanol in dichloromethane. Yield: 80 mg (35%). The product was recrystallized from methanol. Mp.: 125-126° C. MS (ESI) m/z 342.7 (M+1)⁺, 343.8 (M+2)⁺. ¹H NMR (CDCl₃): δ 1.55-2.15 (m, 8H, 4 CH₂); 2.24 (s, 3H, CH₃); 3.21-3.33 (m, 1H, CH); 7.07 (d, 2H, J=8.0 Hz, Ar); 7.21-7.28 (m, 1H, Ar); 7.46 (t, 1H, J=7.3 Hz, Ar); 7.74-7.87 (m, 4H, Ar). ¹³C NMR 400 MHz (CDCl₃): δ 20.7, 24.4, 29.7, 32.4, 39.6, 62.5, 115.8, 120.7, 122.6, 126.7, 127.3, 129.4, 132.4, 137.1, 143.8, 147.5, 157.1. Anal. (C₂₂H₂₂N₄.1.7H₂O) C, H, N.

N-(4-Methoxy-phenyl)-2-cyclopentyl-1H-imidazo[4,5-c]quinolin-4-amine (compound 32)

Scale: 0.7 mmol Eluent for column chromatography was 1% methanol in dichloromethane. Yield: 90 mg (38%). The product was recrystallized from methanol. Mp.: 106-107° C.; MS (ESI) m/z 358.8 (M+1)⁺. ¹H NMR (CDCl₃): δ 1.71-2.29 (m, 8H, 4CH₂); 3.22-3.38 (m, 1H, CH); 3.65 (s, 3H, OCH₃); 6.80-6.84 (m, 2H, Ar); 7.26 (t, 1H, J=8.0 Hz, Ar); 7.46 (t, 1H, J=7.3 Hz, Ar); 7.76-7.93 (m, 4H, Ar). ¹³C NMR 400 MHz (CDCl₃): δ 25.5, 32.5, 39.6, 53.4, 55.4, 114.2, 114.8, 116.5, 120.4, 122.1, 122.4, 127.0, 127.2, 133.1, 144.0, 147.8, 155.4, 156.7. Anal. (C₂₂H₂₂N₄O.CH₃OH) C, H, N.

N-(3,4-Dichloro-phenyl)-2-cyclopentyl-1H-imidazo[4,5-c]quinolin-4-amine (compound 33)

Scale: 0.7 mmol Eluent for column chromatography was dichloromethane. Polarity was slowly increased with methanol till 2%. Yield: 150 mg (54%). The product was recrystallized from methanol. Mp.: 114-115° C. MS (ESI) m/z 396.5 (M+1)⁺, 398.5 (M+2)⁺, 400.5 (M+3)⁺. ¹H NMR (CDCl₃): δ 1.68-2.29 (m, 8H, 4CH₂); 3.29-3.43 (m, 1H, CH); 7.33 (t, 2H, J=8.8 Hz, Ar); 7.54 (t, 1H, J=8.0 Hz, Ar); 7.78 (t, 2H, J=8.0 Hz, Ar); 7.99 (d, 1H, J=8.0 Hz, Ar); 8.44 (s, 1H, Ar); 9.62 (broad s, 1H, NH). Anal. (C₂₁H₁₈Cl₂N₄.2.2H₂O) C, H, N.

N-(4-Chloro-phenyl)-2-cyclopentyl-1H-imidazo[4,5-c]quinolin-4-amine (compound 34)

Scale: 1.0 mmol Eluent for column chromatography was 0.5-2% methanol in dichloromethane. Yield: 120 mg (33%). The product was recrystallized from methanol. Mp.: 189-190° C. MS (ESI) m/z 362.7 (M+1)⁺, 365.0 (M+3)⁺. ¹H NMR (CDCl₃): δ 1.67-2.25 (m, 8H, 4CH₂); 3.28-3.43 (m, 1H, CH); 7.27-7.39 (m, 3H, Ar); 7.49-7.59 (m, 1H, Ar); 7.71-7.79 (m, 1H, Ar); 7.97 (t, 3H, J=8.0 Hz, Ar); 8.46 (broad s, 1H, NH). Anal. (C₂₁H₁₉ClN₄.1.5H₂O) C, H, N.

N-(3-Methanol-phenyl)-2-cyclopentyl-1H-imidazo[4,5-c]quinolin-4-amine (compound 35)

Scale: 0.4 mmol Eluent for column chromatography was ethyl acetate:petroleum ether=50:50, later increased to 70:30 respectively. Yield: 33 mg (25%). The product was recrystallized from methanol giving off-white crystals. Mp.: 228-230° C. MS (ESI) m/z 359.0 (M+1)⁺. ¹H NMR (CDCl₃/CD₃OD): δ 1.63-2.16 (m, 8H, 4CH₂); 3.23-3.24 (m, 1H, CH); 3.95-4.05 (q, 2H, J=7.3 Hz, CH₂); 6.93 (d, 1H, J=8.0 Hz, Ar); 7.18-7.28 (m, 3H, Ar); 7.39 (t, 1H, J=7.3 Hz, Ar); 7.72-7.92 (m, 3H, Ar, OH). Anal. (C₂₂H₂₂N₄O.0.5CH₃OH) C, H, N.

N-([3,4-c]Indan)-2-cyclopentyl-1H-imidazo[4,5-c]quinolin-4-amine (compound 36)

Scale: 0.4 mmol Eluent for column chromatography was 1% methanol in dichloromethane. Yield: 120 mg (81%). The product was recrystallized from methanol giving light brown crystals. Mp.: 142-145° C. MS (ESI) m/z 369.0 (M+1)⁺. ¹H NMR (CDCl₃): δ 1.15-1.34 (m, 2H, CH₂); 1.65-2.19 (m, 8H, 4CH₂); 2.76 (t, 4H, J=7.3 Hz, 2 CH₂); 3.24-3.27 (m, 1H, CH); 7.06 (d, 1H, J=8.0 Hz, Ar); 7.22-7.29 (m, 1H, Ar); 7.40-7.49 (m, 2H, Ar); 7.73 (s, 1H, Ar); 7.85-7.96 (m, 2H, Ar). Anal. (C₂₄H₂₄N₄.1.2H₂O) C, H, N.

N-(1H-indazol-6-yl)-2-cyclopentyl-1H-imidazo[4,5-c]quinolin-4-amine (compound 37)

Scale: 0.4 mmol Eluent for column chromatography was ethylacetate:petroleumether=80:20. Yield: 110 mg (74%). The product was recrystallized from ethyl acetate:petroleum ether=50:50 giving off-white crystals. Mp.: 235-236° C. MS (ESI) m/z 368.8 (M+1)⁺. ¹H NMR (CD₃OD): δ 1.70-2.38 (m, 8H, 4CH₂); 3.23-3.50 (m, 1H, CH); 7.31-7.38 (m, 1H, Ar);

7.47-7.60 (m, 2H, Ar); 7.71-7.75 (m, 1H, Ar); 7.82-7.86 (m, 1H, Ar); 8.01-8.08 (m, 2H, Ar); 8.68 (s, 1H, Ar). Anal. ($C_{22}H_{20}N_6 \cdot 1.5H_2O$) C, H, N.

N-(4-Methoxy-benzyl)-2-cyclopentyl-1H-imidazo[4,5-c]quinolin-4-amine (compound 38)

Scale: 0.4 mmol Eluent for column chromatography was diisopropylether. Yield: 33 mg (22%). The product was recrystallized from methanol giving white crystals. Mp.: 245-247° C. MS (ESI) m/z 372.9 (M+1)$^+$. $^1$H NMR (CD$_3$OD): δ 1.72-2.30 (m, 8H, 4CH$_2$); 3.26-3.41 (m, 1H, CH); 3.77 (s, 3H, OCH$_3$); 4.76 (s, 2H, CH$_2$); 6.87-6.92 (m, 2H, Ar); 7.23-7.49 (m, 4H, Ar); 7.78 (d, 1H, J=8.8 Hz, Ar); 8.00 (d, 1H, J=7.3 Hz, Ar). Anal. ($C_{23}H_{24}N_4O$) C, H, N.

N-(1H-Indol-6-yl)-2-cyclopentyl-1H-imidazo[4,5-c]quinolin-4-amine (compound 39)

Scale: 0.4 mmol Eluent for column chromatography was ethyl acetate:petroleum ether=20:80, increased to 30:70. Yield: 30 mg (20%). The product was recrystallized from methanol giving light grey crystals. Mp.: 260-261° C. MS (ESI) m/z 368.0 (M+1)$^+$. $^1$H NMR (CD$_3$OD): δ 1.79-2.29 (m, 8H, 4CH$_2$); 3.30-3.46 (m, 1H, CH); 6.45 (d, 1H, J=2.9 Hz, Ar); 7.23-7.50 (m, 5H, Ar); 7.77 (d, 1H, J=7.8 Hz, Ar); 8.01 (d, 1H, J=8.0 Hz, Ar); 8.20 (s, 1H, Ar). Anal. ($C_{23}H_{21}N_5$) C, H, N.

N-(Benzyl)-2-cyclopentyl-1H-imidazo[4,5-c]quinolin-4-amine (compound 40)

Scale: 0.8 mmol Eluent for column chromatography was 2% methanol in dichloromethane. Yield: 0.07 mg (25%). The product was oily. $^1$H NMR (CDCl$_3$): δ 1.50-2.11 (m, 8H, 4 CH$_2$); 3.14-3.31 (m, 1H, CH); 4.85 (s, 2H, CH$_2$); 6.25 (broad s, 2H, 2 NH); 7.08-7.20 (m, 6H, Ar); 7.38 (t, 1H, J=8.8 Hz, Ar); 7.87 (d, 1H, J=8.8 Hz, Ar); 8.09 (d, 1H, J=8.0 Hz, Ar). $^{13}$C NMR (CDCl$_3$): δ 25.3, 32.3, 39.7, 45.4, 116.1, 121.3, 122.2, 125.3, 127.0, 127.4, 128.1, 138.1, 143.3, 144.0, 149.7, 157.4, 160.6. Anal. ($C_{22}H_{22}N_4$) C, H, N.

N-(Phenylethyl)-2-cyclopentyl-1H-imidazo[4,5-c]quinolin-4-amine (compound 41)

Scale: 0.8 mmol Eluent for column chromatography was 1% methanol (increased to 4%) in dichloromethane. Yield: 160 mg (56%). The product was product was recrystallized from absolute methanol giving off-white crystals: mp 95-97° C.; MS (ESI) m/z 356.9 (M+1)$^+$, 357.7 (M+2)$^+$, 359.0 (M+3)$^+$. $^1$H NMR (CD$_3$OD): δ 1.75-2.21 (m, 8H, 4 CH$_2$); 3.02 (t, 2H, J=8.0 Hz, CH$_2$); 3.30-3.38 (m, 1H, CH); 3.89 (t, 2H, J=8.0 Hz, CH$_2$); 7.15-7.45 (m, 7H, Ar); 7.76 (d, 1H, J=8.8 Hz, Ar); 7.97 (d, 1H, J=6.3 Hz, Ar). $^{13}$C NMR (CD$_3$OD): δ 27.6, 29.0, 34.9, 41.6, 116.8, 119.1, 121.1, 121.6, 124.2, 125.1, 128.2, 128.3, 131.2, 133.3, 141.7, 144.4, 147.3, 160.1. Anal. ($C_{23}H_{24}N_4$) C, H, N.

N-(3,4-Dichloro-phenyl)-2-cycloheptyl-1H-imidazo[4,5-c]quinolin-4-amine (compound 42)

Scale: 0.8 mmol Eluent for column chromatography was ethyl acetate:petroleum ether=70:90, increased to 100% ethyl acetate. Yield: 164 mg (50%). The product was recrystallized from methanol giving off-white crystals. Mp.: 236-238° C. MS (ESI) m/z 424.9 (M+1)$^+$, 426.8 (M+2)$^+$, 428.1 (M+3)$^+$. $^1$H NMR (CDCl$_3$/CD$_3$OD 9/1, v/v): δ 1.62-2.00 (m, 10H, 5 CH$_2$); 2.17-2.24 (m, 2H, CH$_2$); 3.09-3.23 (m, 1H, CH); 7.32-7.39 (m, 2H, Ar); 7.50-7.58 (m, 1H, Ar); 7.71-7.85 (m, 2H, Ar); 7.98 (d, 1H, J=8.0 Hz, Ar); 8.41 (s, 1H, Ar). $^{13}$C NMR (DMSO-d$_6$): δ 26.2, 27.7, 33.4, 40.2, 115.2, 119.3, 120.2, 121.0, 122.0, 122.9, 127.0, 128.3, 130.1, 130.6, 134.2, 141.6, 142.7, 146.8, 158.6. Anal. ($C_{23}H_{22}Cl_2N_4 \cdot 1.3H_2O$) C, H, N.

N-(3,4-Dichloro-phenyl)-2-furyl-1H-imidazo[4,5-c]quinolin-4-amine (compound 43)

Scale: 0.4 mmol Eluent for column chromatography was ethyl acetate:petroleum ether=20:80. Yield: 96 mg (64%). The product was recrystallized from methanol giving orange crystals. Mp.: 135-138° C. MS (ESI) m/z 394.7 (M+1)$^+$, 396.7 (M+3)$^+$. $^1$H NMR (CD$_3$OD): δ 6.64-6.67 (m, 1H, Ar); 7.10 (d, 1H, J=3.7 Hz, Ar); 7.21-7.44 (m, 4H, Ar); 7.65-7.72 (m, 2H, Ar); 7.95 (d, 1H, J=8.0 Hz, Ar); 8.43-8.44 (m, 1H, Ar). $^{13}$C NMR (DMSO-d$_6$): δ 110.6, 112.6, 115.3, 119.5, 120.4, 121.5, 122.2, 123.2, 127.1, 127.6, 128.2, 130.1, 130.3, 130.6, 134.6, 141.5, 142.3, 143.2, 144.7, 145.1, 146.9. Anal. ($C_{20}H_{12}Cl_2N_4O \cdot 0.5H_2O$) C, H, N.

N-(3,4-Dichloro-phenyl)-2-cyclobutyl-1H-imidazo[4,5-c]quinolin-4-amine (compound 44)

Scale: 0.7 mmol Eluent for column chromatography was ethyl acetate:petroleum ether=20:80. Yield: 121 mg (48%). The product was recrystallized from methanol:ethyl acetate=20:80 giving off-white crystals. Mp.: 131-134° C. MS (ESI) m/z 382.8 (M+1)$^+$. $^1$H NMR (CD$_3$OD): δ 2.00-2.22 (m, 2H, CH$_2$); 2.42-2.56 (m, 4H, 2 CH$_2$); 3.72-3.89 (m, 1H, CH); 7.26-7.33 (m, 2H, Ar); 7.47-7.54 (m, 1H, Ar); 7.64-7.69 (m, 1H, Ar); 7.88-7.96 (m, 2H, Ar); 8.30 (s, 1H, Ar). Anal. ($C_{20}H_{16}Cl_2N_4 \cdot 1.0$ MeOH) C, H, N.

N-(3,4-Dichloro-phenyl)-2-cyclohexyl-1H-imidazo[4,5-c]quinolin-4-amine (compound 45)

Scale: 0.9 mmol Eluent for column chromatography was ethyl acetate:petroleum ether=15:85, increased to 30:70. Yield: 160 mg (44%). The product was recrystallized from methanol:ethyl acetate=1:99 giving off-white crystals. Mp.: 237-240° C. MS (ESI) m/z 410.8 (M+1)$^+$, 412.7 (M+2)$^+$, 414.7 (M+3)$^+$. $^1$H NMR (CD$_3$OD): δ 1.40-2.00 (m, 8H, 4 CH$_2$); 2.15-2.28 (m, 2H, CH$_2$); 2.95-3.07 (m, 1H, CH); 7.34-7.56 (m, 4H, Ar); 7.77-7.88 (m, 2H, Ar); 8.52 (s, 1H, Ar). $^{13}$C NMR (DMSO-d$_6$): δ 25.6, 31.6, 38.2, 115.5, 119.2, 120.1, 121.1, 122.0, 123.0, 127.0, 130.1, 130.6, 134.1, 141.6, 142.7, 146.7, 153.2, 157.5. Anal. ($C_{22}H_{20}Cl_2N_4 \cdot 2.1H_2O$) C, H, N.

N-(3,4-Dichloro-phenyl)-2-1H-imidazo[4,5-c]quinolin-4-amine (compound 46)

Scale: 1.0 mmol Eluent for column chromatography was ethyl acetate:petroleum ether=20:80. Yield: 160 mg (50%). The product was recrystallized from ethyl acetate:petroleum ether=30:70 giving white crystals. Mp.: 167-172° C. MS (ESI) m/z 328.9 (M+1)$^+$, 331.0 (M+2)$^+$, 332.0 (M+3)$^+$. $^1$H NMR (CDCl$_3$): δ 7.23-7.36 (m, 2H, Ar); 7.39-7.43 (m, 1H, Ar); 7.62-7.72 (m, 1H, Ar); 7.65-7.95 (m, 3H, Ar); 8.32 (s, 1H, Ar). Anal. ($C_{16}H_{10}Cl_2N_4 \cdot 1.1H_2O$) C, H, N.

N-(3,4-Dichloro-phenyl)-2-pentyl-1H-imidazo[4,5-c]quinolin-4-amine (compound 47)

Scale: 0.2 mmol Eluent for column chromatography was dichloromethane. Yield: 44 mg (73%). The product was recrystallized from ethyl acetate:petroleum ether=50:50 giving white crystals. Mp.: 195-200° C. MS (ESI) m/z 398.9 (M+1)$^+$, 400.8 (M+3)$^+$. $^1$H NMR (CDCl$_3$): δ 0.82-0.97 (m, 3H, CH$_3$); 1.39-1.51 (m, 2H, CH$_2$); 1.81 (m, 4H, 2 CH$_2$); 2.98 (t, 2H, J=8.0 Hz, CH$_2$); 7.33-7.41 (m, 2H, Ar); 7.52-7.60 (m, 1H, Ar); 7.74-7.81 (m, 2H, Ar); 7.99 (d, 1H, J=8.0 Hz, Ar); 8.48 (s, 1H, Ar). Anal. (C$_{21}$H$_{20}$Cl$_2$N$_4$) C, H, N.

Table 1 summarizes the chemical structures and physico-chemical characteristics of the imidazoquinoline derivatives prepared as described above.

TABLE 1

Chemical structure and physico-chemical characteristics

| Nr | Compound | Molecular Formula | MW | Mp (° C.) | MS | Recrystall-ization. solvent |
|----|----------|-------------------|------|-----------|-------|-----------|
| 30 | | C$_{21}$H$_{20}$N$_4$ | 328.42 | 155-157 | 328.9 | MeOH |
| 31 | | C$_{22}$H$_{22}$N$_4$ | 342.45 | 125-126 | 342.7 343.8 | MeOH |
| 32 | | C$_{22}$H$_{22}$N$_4$O | 358.45 | 106-107 | 358.8 | MeOH |
| 33 | | C$_{21}$H$_{18}$Cl$_2$N$_4$ | 397.31 | 114-115 | 396.5 | MeOH |

TABLE 1-continued

Chemical structure and physico-chemical characteristics

| Nr | Compound | Molecular Formula | MW | Mp (° C.) | MS | Recrystall-ization. solvent |
|---|---|---|---|---|---|---|
| 34 | (4-chlorophenylamino, 2-cyclopentyl imidazoquinoline) | $C_{21}H_{19}ClN_4$ | 362.87 | 189-190 | 362.7 | MeOH |
| 35 | (3-hydroxymethylphenylamino, 2-cyclopentyl imidazoquinoline) | $C_{22}H_{22}N_4O$ | 358.45 | 228-230 | 359.0 | MeOH |
| 36 | (indanylamino, 2-cyclopentyl imidazoquinoline) | $C_{24}H_{24}N_4$ | 368.49 | 142-145 | 369.0 | MeOH |
| 37 | (indazolylamino, 2-cyclopentyl imidazoquinoline) | $C_{22}H_{20}N_6$ | 368.44 | 235-236 | 368.8 | 50/50 EA/PE |
| 38 | (4-methoxybenzylamino, 2-cyclopentyl imidazoquinoline) | $C_{23}H_{24}N_4O$ | 372.47 | 245-247 | 372.9 | MeOH |

TABLE 1-continued

Chemical structure and physico-chemical characteristics

| Nr | Compound | Molecular Formula | MW | Mp (° C.) | MS | Recrystall-ization. solvent |
|---|---|---|---|---|---|---|
| 39 | (structure) | $C_{23}H_{21}N_5$ | 367.46 | 260-261 | 368.0 | MeOH |
| 40 | (structure) | $C_{22}H_{22}N_4$ | 342.45 | — | — | oil |
| 41 | (structure) | $C_{23}H_{24}N_4$ | 356.47 | 95-97 | 356.9 357.7 359.0 | MeOH |
| 42 | (structure) | $C_{23}H_{22}Cl_2N_4$ | 425.36 | 236-238 | 424.9 426.8 | MeOH |
| 43 | (structure) | $C_{20}H_{12}Cl_2N_4O$ | 395.25 | 135-138 | 394.7 396.7 | MeOH |

TABLE 1-continued

Chemical structure and physico-chemical characteristics

| Nr | Compound | Molecular Formula | MW | Mp (° C.) | MS | Recrystall-ization. solvent |
|---|---|---|---|---|---|---|
| 44 | (3,4-dichlorophenylamino-2-cyclobutyl-imidazoquinoline) | $C_{20}H_{16}Cl_2N_4$ | 383.28 | 131-134 | 382.8 386.9 | 20/80 MeOH/EA |
| 45 | (3,4-dichlorophenylamino-2-cyclohexyl-imidazoquinoline) | $C_{22}H_{20}Cl_2N_4$ | 411.34 | 237-340 | 410.8 412.7 414.7 | EA + 1% MeOH |
| 46 | (3,4-dichlorophenylamino-imidazoquinoline) | $C_{16}H_{10}Cl_2N_4$ | 329.19 | 167-172 | 328.9 331.0 332.0 | 30/70 PE/EA |
| 47 | (3,4-dichlorophenylamino-2-pentyl-imidazoquinoline) | $C_{21}H_{20}Cl_2N_4$ | 399.33 | 195-200 | 398.9 400.8 | 50/50 EA/PE |

MW: molecular weight (D);
Mp: melting point (° C.);
MS: mass spectrometry data (M + 1, M + 2, M + 3)

Biological Experiments
Material:
[$^{125}$I]N$^6$-(4-amino-3-iodobenzyl)adenosine-5'-N-methyluronamide (I-AB-MECA; 2000 Ci/mmol), [$^3$H]R-PIA (R—N$^6$-[phenylisopropyl]adenosine, 34 Ci/mmol), [$^3$H] CGS21680 (2-[p-(2-carboxyethyl)phenylethylamino]-5'-N-ethylcarboxamido-adenosine, 47 Ci/mmol) and [$^3$H]cyclic AMP (40 Ci/mmol) were from Amersham Pharmacia Biotech (Buckinghamshire, UK).

Cell Culture and Membrane Preparation:

CHO (Chinese hamster ovary) cells expressing the recombinant human ARs (HEK-293 cells were used for the human $A_{2A}AR$) were cultured in DMEM and F12 (1:1) supplemented with 10% fetal bovine serum, 100 units/ml penicillin, 100 ng/ml streptomycin and 2 μmol/ml glutamine. Cells were harvested by trypsinization. After homogenization and suspension, cells were centrifuged at 500 g for 10 min, and the pellet was re-suspended in 50 mM Tris.HCl buffer (pH 7.4) containing 10 mM $MgCl_2$. The suspension was homogenized with an electric homogenizer for 10 sec, and was then re-centrifuged at 20,000 g for 20 min at 4° C. The resultant pellets were resuspended in buffer in the presence of 3 Units/mL adenosine deaminase, and the suspension was stored at −80° C. until the binding experiments. The protein concentration was measured using the Bradford assay.

Binding Assays to the Human $A_1$ and $A_{2A}$ ARs:

For binding to the human $A_1AR$, [$^3$H]R-PIA (2 nM) was incubated with membranes (40 μg/tube) from CHO cells stably expressing the human $A_1AR$ at 25° C. for 60 min in 50 mM Tris.HCl buffer (pH 7.4; $MgCl_2$, 10 mM) in a total assay volume of 200 μL. Nonspecific binding was determined using 10 μM of $N^6$-cyclopentyladenosine. For human $A_{2A}$AR binding, membranes (20 μg/tube) from HEK-293 cells stably expressing the human $A_{2A}$ AR were incubated with 15 nM [$^3$H]CGS21680 at 25° C. for 60 min in 200 μL of 50 mM Tris.HCl, pH 7.4, containing 10 mM $MgCl_2$. N-5′-ethyluronamidoadenosine (10 μM) was used to define nonspecific binding. Reaction was terminated by filtration with GF/B filters.

Binding Assay to the Human $A_3AR$:

Each tube in the competitive binding assay contained 100 μl membrane suspension (20 μg protein), 50 μl [$^{125}$I]-AB-MECA (0.5 nM), and 50 μl of increasing concentrations of the test ligands in Tris.HCl buffer (50 mM, pH 8.0) containing 10 mM $MgCl_2$, 1 mM EDTA. Nonspecific binding was determined using 10 μM of 5′-N-ethylcarboxamidoadenosine in the buffer. The mixtures were incubated at 25° C. for 60 min. Binding reactions were terminated by filtration through Whatman GF/B filters under reduced pressure using a MT-24 cell harvester (Brandell, Gaithersburgh, Md., USA). Filters were washed three times with 9 mL ice-cold buffer. Radioactivity was determined in a Beckman 5500B γ-counter.

Dissociation Kinetics of [$^{125}$I]I-AB-MECA from Human $A_3$ARs:

The dissociation of [$^{125}$I]I-AB-MECA was measured as follows. Membranes (20 μg) were preincubated at 25° C. with 0.5 nM [$^{125}$I]I-AB-MECA, in a total volume of 100 μl of Tris-HCl buffer (50 mM, pH 8.0) containing 10 mM $MgCl_2$, and 1 mM EDTA for 60 min. The dissociation was then initiated by the addition of 3 μM Cl-IB-MECA with or without allosteric modulators. The time course of dissociation of total binding was measured by rapid filtration at appropriate time intervals. Nonspecific binding was measured after 60-min incubation in the presence of 3 μM Cl-IB-MECA. Further assay was as described above.

Cyclic AMP Accumulation Assay:

Intracellular cyclic AMP levels were measured with a competitive protein binding method (Nordstedt and Fredholm, 1990). CHO cells that expressed recombinant human $A_3$ARs were harvested by trypsinization. After centrifugation and resuspension in medium, cells were plated in 24-well plates in 0.5 ml medium. After 24 hr, the medium was removed and cells were washed three times with 1 ml DMEM, containing 50 mM HEPES, pH 7.4. Cells were then treated with agonists and/or test compounds in the presence of rolipram (10 μM) and adenosine deaminase (3 units/ml). After 45 min forskolin (10 μM) was added to the medium, and incubation was continued an additional 15 min. The reaction was terminated by removing the supernatant, and cells were lysed upon the addition of 200 μL of 0.1 M ice-cold HCl. The cell lysate was resuspended and stored at −20° C. For determination of cyclic AMP production, protein kinase A (PKA) was incubated with [$^3$H]cyclic AMP (2 nM) in $K_2HPO_4$/EDTA buffer ($K_2HPO_4$, 150 mM; EDTA, 10 mM), 20 μL of the cell lysate, and 30 μL 0.1 M HCl or 50 μL of cyclic AMP solution (0-16 pmol/200 μL for standard curve). Bound radioactivity was separated by rapid filtration through Whatman GF/C filters and washed once with cold buffer. Bound radioactivity was measured by liquid scintillation spectrometry.

Statistical Analysis

Binding and functional parameters were calculated using Prism 5.0 software (GraphPAD, San Diego, Calif., USA). $IC_{50}$ values obtained from competition curves were converted to $K_i$ values using the Cheng-Prusoff equation. Data were expressed as mean±standard error.

TABLE 2

Potency of 1H-imidazo-[4,5-c]quinolin-4-amine derivatives in binding or activation assays at human $A_1$, $A_{2A}$, $A_{2B}$, and $A_3$ARs and allosteric effects at the human $A_3$AR

| No. | $R_1$ | $R_2$ | $K_i$(h$A_1$AR), nM[a] or % displ. at 10 μM | $K_i$(h$A_{2A}$AR), nM[a] or % displ. at 10 μM | h$A_{2B}$AR[b] % inhib. at 10 μM | $K_i$(h$A_3$AR), nM[a] or % displ. at 10 μM | h$A_3$ARAg. Dissociation[c] at 10 μM | % Increase of efficacy at h$A_3$AR[d] at 10 μM |
|---|---|---|---|---|---|---|---|---|
| 30 | Ph | CP | 3420 ± 230 | 3150 ± 210 | −6.8% | 786 ± 67 (90%) | 174 ± 5 | 138 ± 8 |
| 31 | 4-$CH_3$—Ph | CP | 3850 ± 500 | 5220 ± 320 | −4.1% | 1190 ± 107 (87%) | 153 ± 4 | 128 ± 4 |
| 32 | 4-$CH_3$O—Ph | CP | 4170 ± 730 | >10,000 (16%) | 7.3% | 410 ± 64 (92%) | 166 ± 11 | 132 ± 4 |
| 33 | 3,4-$Cl_2$—Ph | CP | >10,000 (15%) | >10,000 (0%) | −6.7% | 4690 ± 970 (67%) | 144 ± 9 | 141 ± 5 |
| 34 | 4-Cl—Ph | CP | >10,000 (22%) | >10,000 (17%) | −10.2% | 1610 ± 550 (82%) | 159 ± 5 | 136 ± 3 |
| 35 | 3-$HOCH_2$—Ph | CP | 51% | 49% | −4.1% | 56% | 129 ± 15 | 118 ± 4 |
| 36 | 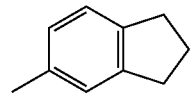 | CP | 21% | 8% | −10.7% | 69% | 108 ± 4 | 111 ± 5 |

TABLE 2-continued

Potency of 1H-imidazo-[4,5-c]quinolin-4-amine derivatives in binding or activation assays at human $A_1$, $A_{2A}$, $A_{2B}$, and $A_3$ARs and allosteric effects at the human $A_3$AR

| No. | $R_1$ | $R_2$ | $K_i(hA_1AR)$, $nM^a$ or % displ. at 10 μM | $K_i(hA_{2A}AR)$, $nM^a$ or % displ. at 10 μM | $hA_{2B}AR^b$ % inhib. at 10 μM | $K_i(hA_3AR)$, $nM^a$ or % displ. at 10 μM | $hA_3ARAg$. Dissociation$^c$ at 10 μM | % Increase of efficacy at $hA_3AR^d$ at 10 μM |
|---|---|---|---|---|---|---|---|---|
| 37 | 6-methyl-1H-indazol-5-yl | CP | 56% | 68% | 5.0% | 67% | 109 ± 3 | 96 ± 2 |
| 38 | 4-CH$_3$O—PhCH$_2$ | CP | 59% | 60% | 0.3% | 80% | 101 ± 13 | 109 ± 3 |
| 39 | 6-methyl-1H-indol-5-yl | CP | 70% | 74% | 10.1% | 89% | 126 ± 9 | 125 ± 2 |
| 40 | PhCH$_2$ | CP | 28% | 77% | −3.4% | 86% | 145 ± 10 | 147 ± 8 |
| 41 | Ph(CH$_2$)$_2$ | CP | 52% | 91% | −11.6% | 84% | 154 ± 7 | 137 ± 4 |
| 42 | 3,4-Cl$_2$—Ph | cycloheptyl | −4% | −2% | −7.3% | 68% | 130 ± 2 | 115 ± 7 |
| 43 | 3,4-Cl$_2$—Ph | furan-2-ylmethyl | −4% | 70% | 9.0% | 78% | 98 ± 3 | 95 ± 4 |
| 44 | 3,4-Cl$_2$—Ph | cyclobutyl | −5% | 0.4% | −5.5% | 52% | 116 ± 3 | 126 ± 3 |
| 45 | 3,4-Cl$_2$—Ph | cyclohexyl | −2% | −1% | −5.6% | 45% | 173 ± 5 | 145 ± 7 |
| 46 | 3,4-Cl$_2$—Ph | H | 1.8% | −0.8% | 10.2% | 39% | 91 ± 7 | 92 ± 4 |
| 47 | 3,4-Cl$_2$—Ph | n-pentyl | 43.9% | −1% | −9.3% | 84% | 116 ± 5 | 102 ± 5 |

$^a$All experiments were performed using adherent CHO (A$_1$ and A$_3$) and HEK293 (A$_{2A}$) cells stably transfected with cDNA encoding the human ARs. Binding at human A$_1$, A$_{2A}$ and A$_3$ ARs in this study was carried out as described in Methods using [$^3$H]R-PIA (2.0 nM), [$^3$H]CGS 21680 (15 nM) or [$^{125}$I]I-AB-MECA (0.5 nM) as a radioligand. Values from the present study are expressed as mean ± s.e.m., n = 3-5. Percentage inhibition at A$_1$, A$_{2A}$, or A$_3$ receptors is expressed as the mean value from 2-4 separate experiments with similar results performed in duplicate.
$^b$A$_{2B}$ receptor: effect of compounds at 10 μM on NECA (150 nM)-induced cyclic AMP accumulation from one experiment performed in triplicate; the inhibition of CGS15943 (10 μM) was expressed as 100%.
$^c$dissociation: % decrease of dissociation at 30 min; the residual binding of [$^{125}$I]AB-MECA after 30 min of dissociation was expressed as 100%.
$^d$increase of efficacy: compared to maximal effect by 2-Cl-IB-MECA alone (control = 100%)

Further, several additional 1H-imidazo-[4,5-c]quinolin-4-amine derivatives were synthesized in accordance with the procedure described above. the potency of these derivatives is provided in Tables 3 and 4.

TABLE 3

Potency of 1H-imidazo-[4,5-c]quinolin-4-amine derivatives in binding assays at human $A_1$, $A_{2A}$, and $A_3$ARs expressed in CHO cells and allosteric effects at the human $A_3$AR.

| No. | R | Ki (hA$_1$AR), nM$^a$ or % displ. at 10 μM | hA$_{2A}$AR, % displ. at 10 μM | $K_i$(hA$_3$AR), nM$^a$ or % displ. at 10 μM | hA$_3$RAg. Dissociation (%)$^c$ at 10 μM | Enhancement of GTPγS binding (%) at hA$_3$AR$^e$ at 10 μM | Relative efficacy (%) at hA$_3$AR$^e$ at 10 μM (GTPγS binding) in absence of agonist |
|---|---|---|---|---|---|---|---|
| 48 | cyclobutyl | <10% | <10% | 52% | 116 ± 3 | 126 ± 3 | |

TABLE 3-continued

Potency of 1H-imidazo-[4,5-c]quinolin-4-amine derivatives in binding assays at human $A_1$, $A_{2A}$, and $A_3$ARs expressed in CHO cells and allosteric effects at the human $A_3$AR.

| No. | R | Ki (hA$_1$AR), nM$^a$ or % displ. at 10 μM | hA$_{2A}$AR, % displ. at 10 μM | K$_i$ (hA$_3$AR), nM$^a$ or % displ. at 10 μM | hA$_3$RAg. Dissociation (%)$^c$ at 10 μM | Enhancement of GTPγS binding (%) at hA$_3$AR$^e$ at 10 μM | Relative efficacy (%) at hA$_3$AR$^e$ at 10 μM (GTPγS binding) in absence of agonist |
|---|---|---|---|---|---|---|---|
| 49 | cyclopentyl | 15% | <10% | 4690 ± 970 (67%) | 144 ± 9 | 141 ± 5 | |
| 45 | cyclohexyl | <10% | <10% | 45% | 173 ± 5 | 194 ± 11, 177 | 6 |
| 50 | cycloheptyl | <10% | <10% | 68% | 130 ± 2 | 115 ± 7 | |
| 51 | tetrahydropyranyl | 45 ± 11% | 39 ± 2% | 37 ± 23% | 112.2 ± 1.4 | 116 | 7 |
| 52 | norbornyl | 78 ± 12% | 57 ± 2% | −11 ± 8% | 134.9 ± 4.4 | 200 | 22 |
| 53 | norbornyl | 65 ± 9% | 6 ± 1% | 54 ± 3% | 140.0 ± 1.9 | 180 | 5 |
| 54 | phthalimidocyclohexyl | 21 ± 4% | 16 ± 1% | −13 ± 4% | 109.2 ± 10.1 | 113 | 8 |
| 55 | 4-aminocyclohexyl | 32 ± 16% | 9 ± 2% | −5 ± 9% | 91.0 ± 2.4 | 104 | 7 |
| 56 | N-Bz piperidinyl | 32 ± 5% | −3 ± 2% | 23 ± 2% | 78.2 ± 2.2 | 65 | 2 |
| 57 | N-Bn piperidinyl | 43 ± 8% | −19 ± 4% | 11 ± 4% | 110.9 ± 5.7 | 111 | 6 |

TABLE 3-continued

Potency of 1H-imidazo-[4,5-c]quinolin-4-amine derivatives in binding assays at human $A_1$, $A_{2A}$, and $A_3$ARs expressed in CHO cells and allosteric effects at the human $A_3$AR.

| No. | R | Ki (hA$_1$AR), nM[a] or % displ. at 10 μM | hA$_{2A}$AR, % displ. at 10 μM | K$_i$ (hA$_3$AR), nM[a] or % displ. at 10 μM | hA$_3$RAg. Dissociation (%)[c] at 10 μM | Enhancement of GTPγS binding (%) at hA$_3$AR[e] at 10 μM | Relative efficacy (%) at hA$_3$AR[e] at 10 μM (GTPγS binding) in absence of agonist |
|---|---|---|---|---|---|---|---|
| 58 | (4-piperidinyl-NH) | 34 ± 3% | 7 ± 1% | 4 ± 5% | 89.9 ± 3.6 | 83 | 2 |
| 59 | (adamantyl) | not yet determined | | | | not yet determined | |
| 60 | (adamantyl) | not yet determined | | | | not yet determined | |

[a]All experiments were performed using adherent CHO cells stably transfected with cDNA encoding the human ARs. Binding at human $A_1$, $A_{2A}$ and $A_3$ARs in this study was carried out as described in Experimental Procedures using [$^3$H]R-PIA, [$^3$H]CGS 21680 or [$^{125}$I]I-AB-MECA as a radioligand. Values from the present study are expressed as mean ± s.e.m., n = 3-5. Percentage inhibition at $A_1$, $A_{2A}$, or $A_3$ receptors is expressed as the mean value from 2-4 separate experiments with similar results performed in duplicate.
[b]Values from Göblyös et al.
[c]dissociation: % decrease of [$^{125}$I]I-AB-MECA dissociation at 30 min (control = 100%)
[d]increase of efficacy; compared to maximal effect by 2-Cl-IB-MECA alone (control)
[e]10 μM Cl-IB-MECA alone = 100%

TABLE 4

Potency of 1H-imidazo-[4,5-c]quinolin-4-amine derivatives in binding assays at human $A_1$ and $A_{2A}$ ARs expressed in CHO cells and allosteric effects at the human $A_3$AR.[a]

| No. (MRS no.) | R | K$_i$(hA$_1$AR), nM[a] or % displ. at 10 μM | K$_i$(hA$_{2A}$AR), nM[a] or % displ. at 10 μM | Enhancement of GTPγS binding (%) at hA3AR d at 10 μM |
|---|---|---|---|---|
| 45 | 3,4-Cl$_2$—PhNH | <10% | <10% | 194 ± 11 |
| 61 | 3-Cl—PhNH | 53 ± 4% | 43 ± 4% | 197 ± 12 |
| 62 | 3,5-Cl$_2$—PhNH | 16 ± 3% | <10% | 195 ± 15 |
| 63 | 2,4-Cl$_2$—PhNH | 48 ± 1% | 67 ± 2% | 163 ± 15 |
| 64 | 3,4-F$_2$—PhNH | 15 ± 5% | 27 ± 7% | 180 ± 15 |
| 65 | 3,5-F$_2$—PhNH | not determined | | not determined |

TABLE 4-continued

Potency of 1H-imidazo-[4,5-c]quinolin-4-amine derivatives in binding assays at human $A_1$ and $A_{2A}$ ARs expressed in CHO cells and allosteric effects at the human $A_3AR$.[a]

| No. (MRS no.) | R | $K_i(hA_1AR)$, $nM^a$ or % displ. at 10 μM | $K_i(hA_{2A}AR)$, $nM^a$ or % displ. at 10 μM | Enhancement of GTP☐S binding (%) at hA3AR d at 10 μM |
|---|---|---|---|---|
| 66 | 3,5-(CF$_3$)$_2$—PhNH | not determined | | not determined |
| 67 | 3,4-(CN)$_2$—PhNH | not determined | | not determined |
| 67 | 3,4-(O)$_2$CH$_2$—PhNH[e] | 65 ± 3% | 49 ± 1% | 157 ± 6 |

[a] All experiments were performed using adherent CHO cells stably transfected with cDNA encoding the human ARs. Binding at human $A_1$, $A_{2A}$ and $A_3$ARs in this study was carried out as described in Experimental Procedures using [$^3$H]R-PIA, [$^3$H]CGS 21680 or [$^{125}$I]I-AB-MECA as a radioligand. Values from the present study are expressed as mean ± s.e.m., n = 3-5. Percentage inhibition at $A_1$, $A_{2A}$, or $A_3$ receptors is expressed as the mean value from 2-4 separate experiments with similar results performed in duplicate.
[b] $A_{2B}AR$: effect of compounds at 10 μM on NECA (150 nM)-induced cyclic AMP accumulation from one experiment performed in triplicate, CGS15943 (10 μM) = 100%.
[c] dissociation: % decrease of [$^{125}$I]I-AB-MECA dissociation at 30 min (control = 100%)
[d] increase of efficacy: compared to maximal effect by 2-Cl-IB-MECA alone (control)
[e] methylenedioxo substituent at the 3 and 4 poisitions of the phenyl ring, namely, a 5 memebered diether ring substituent In Tables 2 to 4 the effects of the imidazoquinoline derivatives at the orthosteric sites of all four adenosine receptor subtypes were listed, together with their effects on the allosteric site on the human adenosine $A_3$ receptor. Many compounds display little if any affinity for the orthosteric binding sites, particularly on the adenosine $A_1$, $A_{2A}$ and $A_{2B}$ receptor, especially when $R_1$=3,4-Cl$_2$-phenyl (namely a 3,4-dichlororo phenyl substituent). Also the orthosteric binding site on the adenosine $A_3$ receptor accommodates the imidazoquinoline derivatives rather poorly. The best separation between orthosteric and allosteric recognition was found with compound 45. Thus, this compound was selected for further in vivo assays.

In Vivo Evaluation of Imidazoquinoline Derivative 45 Potency as an $A_3$AM:

A. Inhibitory Activity of Imidazoquinoline Derivative 45 on Myeloid System:

A stock solution of imidazoquinoline derivative 45 was prepared by dissolving the same in DMSO. Further dilutions for treatment were performed in PBS. As a control, an equivalent amount of DMSO in PBS was used.

To test the effect of imidazoquinoline derivative 45 on the myeloid system, the compound was orally administered at a dose of 100 μg/kg, thrice daily to ICR mice, for two consecutive days. Blood samples were withdrawn 24 and 48 hours after the last drug administration. A differential blood count was performed.

Figure 2A:
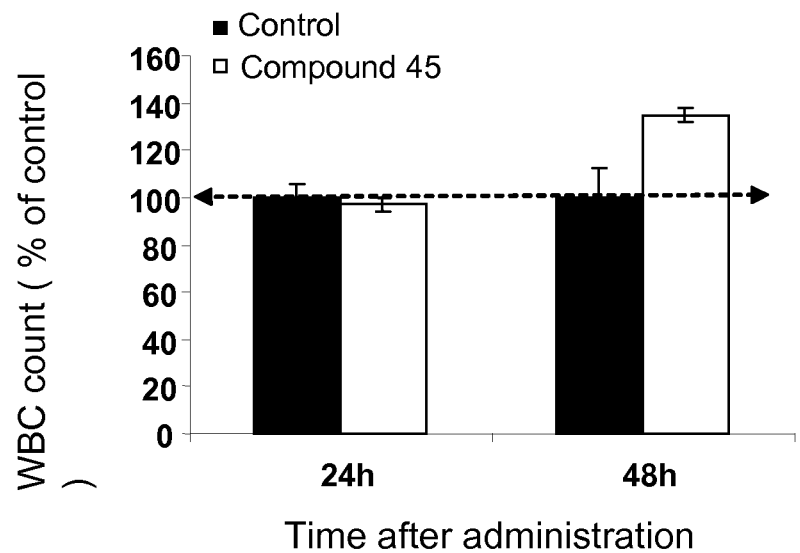
FIGS. 2A-2B are bar graphs showing the effect of imidazoquinoline derivative No. 45 on the number of white blood cells (WBC, FIG. 2A) and neutrophils (FIG. 2B) in naïve mice as compared to control.
Figure 2B:
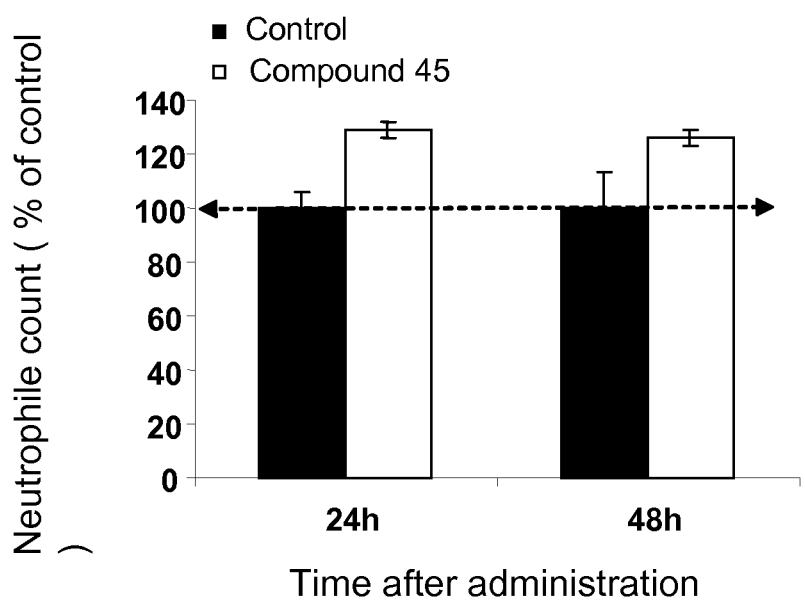

The results presented in FIGS. 2A-2B show that imidazoquinoline derivative 45 enhanced the myeloid system of naïve mice, which was demonstrated by the increased number of white blood cells (WBC) and neutrophils following treatment therewith.

B. Effect of Imidazoquinoline Derivative 45 on the Development of Adjuvant Induced Arthritis AIA:

Adjuvant induced arthritis model (model for rheumatoid arthritis (RA)) was established in rats by immunizing the animals with an emulsion contacting *Mycobacterium tuberculosis* in Freund's adjuvant (Animal Models for Autoimmune and Inflammatory disease:Adjuvant Arthritis in the Rat. Current Protocols in Immunology, Supplement 19, page 15.4.2.). Treatment with imidazoquinoline derivative 45 was initiated upon onset of disease. The imidazoquinoline derivative 45 was administered orally twice daily at a dose of 100 μg/kg.

Figure 3:
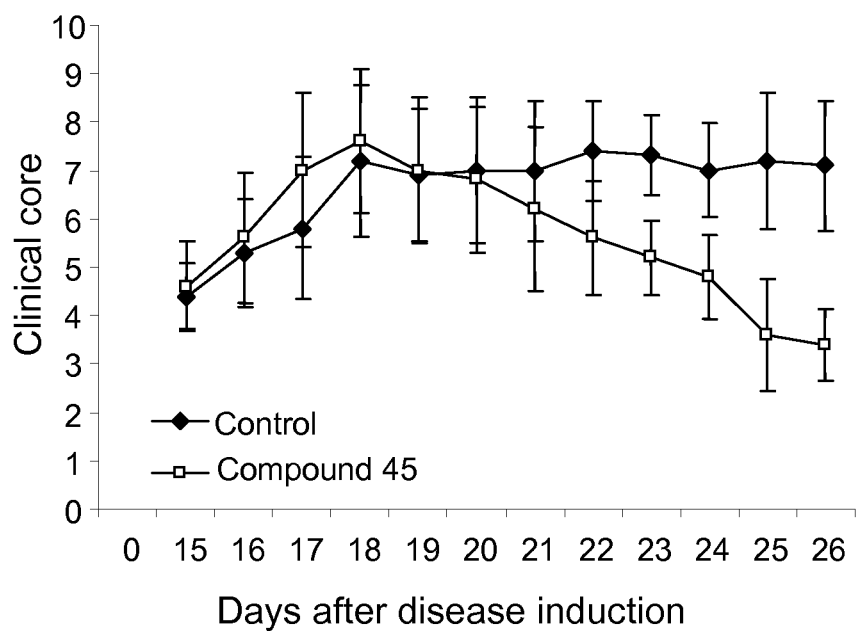
FIG. 3 is a graph showing the reduction in clinical score following treatment with imidazoquinoline derivative 45 a compared to the control.

Evaluation of disease development was carried out daily, starting upon onset of disease until the end of the study. Intensity of arthritis was scored by grading each paw from 0-4 on erythema, swelling and deformity of the joint, every day: 0=no erythema or swelling; 1=slight erythema or swelling of one of the toes or fingers; 2=erythema and swelling of more than one toe or finger; 3=erythema and swelling of the ankle or wrist; 4=complete erythema and swelling of toes or fingers and ankles or wrist, and inability to bend the ankle or wrist. All scores of the four legs from each rat are added to give up to a maximum arthritic score of 16. The results are presented in FIG. 3 which show the reduction in clinical score following treatment with imidazoquinoline derivative 45.

The results presented above suggest that the imidazoquinoline derivative and in the particular example imidazoquinoline derivative 45 may have a dual effect, on the one hand of enhancing the myeloid system and on the other hand, as a remedy for conditions such as RA.

The invention claimed is:

1. An imidazoquinoline derivative selected from the group consisting of
N-(4-Methoxy-phenyl)-2-cyclopentyl-1H-imidazo[4,5-c]quinolin-4-amine,
N-(3,4-Dichloro-phenyl)-2-cyclopentyl-1H-imidazo[4,5-c]quinolin-4-amine,
N-(4-Chloro-phenyl)-2-cyclopentyl-1H-imidazo[4,5-c]quinolin-4-amine,
N-(3-Methanol-phenyl)-2-cyclopentyl-1H-imidazo[4,5-c]quinolin-4-amine,
N-([3,4-c]Indan)-2-cyclopentyl-1H-imidazo[4,5-c]quinolin-4-amine,
N-(1H-indazol-6-yl)-2-cyclopentyl-1H-imidazo[4,5-c]quinolin-4-amine, N-(4-Methoxy-benzyl)-2-cyclopentyl-1H-imidazo[4,5-c]quinolin-4-amine,
N-(1H-Indol-6-yl)-2-cyclopentyl-1H-imidazo[4,5-c]quinolin-4-amine,
N-(3,4-Dichloro-phenyl)-2-cycloheptyl-1H-imidazo[4,5-c]quinolin-4-amine,
N-(3,4-Dichloro-phenyl)-2-furyl)-1H-imidazo[4,5-c]quinolin-4-amine,
N-(3,4-Dichloro-phenyl)-2-cyclobutyl-1H-imidazo[4,5-c]quinolin-4-amine,
N-(3,4-Dichloro-phenyl)-2-cyclohexyl-1H-imidazo[4,5-c]quinolin-4-amine,
N-(3,4-Dichloro-phenyl)-2--1H-imidazo[4,5-c]quinolin-4-amine, and
N-(3,4-Dichloro-phenyl)-2-pentyl-1H-imidazo[4,5-c]quinolin-4-amine.

2. An imidazoquinoline derivative selected from the group consisting of
N-(3,4-Dichloro-phenyl)-2-furyl)-1H-imidazo[4,5-c]quinolin-4-amine,
N-(3,4-Dichloro-phenyl)-2--1H-imidazo[4,5-c]quinolin-4-amine,
N-(3,4-Dichloro-phenyl)-2-pentyl-1H-imidazo[4,5-c]quinolin-4-amine,
N-(3,4-Dichloro-phenyl)-2-cyclopentyl-1H-imidazo[4,5-c]quinolin-4-amine,
N-(3,4-Dichloro-phenyl)-2-cycloheptyl-1H-imidazo[4,5-c]quinolin-4-amine,
N-(3,4-Dichloro-phenyl)-2-cyclobutyl-1H-imidazo[4,5-c]quinolin-4-amine, and
N-(3,4-Dichloro-phenyl)-2-cyclohexyl-1H-imidazo[4,5-c]quinolin-4-amine.

3. A pharmaceutical composition comprising as an active ingredient an imidazoquinoline derivative as claimed in claim 1.

4. A pharmaceutical composition comprising:
an active ingredient selected from the group consisting of
N-(4-Methoxy-phenyl)-2-cyclopentyl-1H-imidazo[4,5-c]quinolin-4-amine,
N-(3,4-Dichloro-phenyl)-2-cyclopentyl-1H-imidazo[4,5-c]quinolin-4-amine,
N-(4-Chloro-phenyl)-2-cyclopentyl-1H-imidazo[4,5-c]quinolin-4-amine,
N-(3-Methanol-phenyl)-2-cyclopentyl-1H-imidazo[4,5-c]quinolin-4-amine,
N-([3,4-c]Indan)-2-cyclopentyl-1H-imidazo[4,5-c]quinolin-4-amine,
N-(1H-indazol-6-yl)-2-cyclopentyl-1H-imidazo[4,5-c]quinolin-4-amine,
N-(4-Methoxy-benzyl)-2-cyclopentyl-1H-imidazo[4,5-c]quinolin-4-amine,
N-(1H-Indol-6-yl)-2-cyclopentyl-1H-imidazo[4,5-c]quinolin-4-amine,
N-(3,4-Dichloro-phenyl)-2-cycloheptyl-1H-imidazo[4,5-c]quinolin-4-amine,
N-(3,4-Dichloro-phenyl)-2-furyl)-1H-imidazo[4,5-c]quinolin-4-amine,
N-(3,4-Dichloro-phenyl)-2-cyclobutyl-1H-imidazo[4,5-c]quinolin-4-amine,
N-(3,4-Dichloro-phenyl)-2-cyclohexyl-1H-imidazo[4,5-c]quinolin-4-amine,
N-(3,4-Dichloro-phenyl)-2--1H-imidazo[4,5-c]quinolin-4-amine, and
N-(3,4-Dichloro-phenyl)-2-pentyl-1H-imidazo[4,5-c]quinolin-4-amine; and
one or more pharmaceutically acceptable excipients.

5. The pharmaceutical composition of claim 4, wherein the active ingredient is selected from the group consisting of
N-(3,4-Dichloro-phenyl)-2-cyclopentyl-1H-imidazo[4,5-c]quinolin-4-amine,
N-(3,4-Dichloro-phenyl)-2-cycloheptyl-1H-imidazo[4,5-c]quinolin-4-amine,
N-(3,4-Dichloro-phenyl)-2-cyclobutyl-1H-imidazo[4,5-c]quinolin-4-amine,
N-(3,4-Dichloro-phenyl)-2-cyclohexyl-1H-imidazo[4,5-c]quinolin-4-amine,
N-(3,4-Dichloro-phenyl)-2-furyl)-1H-imidazo[4,5-c]quinolin-4-amine,
N-(3,4-Dichloro-phenyl)-2--1H-imidazo[4,5-c]quinolin-4-amine, and
N-(3,4-Dichloro-phenyl)-2-pentyl-1H-imidazo[4,5-c]quinolin-4-amine.

6. The pharmaceutical composition of claim 4, wherein the active ingredient is N-(3,4-Dichloro-phenyl)-2-cyclohexyl-1H-imidazo[4,5-c]quinolin-4-amine.

* * * * *